United States Patent
Ji et al.

(10) Patent No.: US 11,905,331 B2
(45) Date of Patent: Feb. 20, 2024

(54) ANTIBODY BINDING SPECIFICALLY TO CD40 AND USE THEREOF

(71) Applicant: Kumho HT, Inc., Gwangju (KR)

(72) Inventors: Gil Yong Ji, Seoul (KR); Kwon Pyo Hong, Cheongju-si (KR); Eui Sup Lee, Seoul (KR); Yoo Ri Moon, Seoul (KR); Sangsoon Yoon, Seoul (KR)

(73) Assignee: KUMHO HT, INC., Gwangju (KR)

( * ) Notice: Subject to any disclaimer, the term of this patent is extended or adjusted under 35 U.S.C. 154(b) by 1318 days.

(21) Appl. No.: 16/348,284

(22) PCT Filed: Nov. 10, 2017

(86) PCT No.: PCT/KR2017/012747
§ 371 (c)(1),
(2) Date: May 8, 2019

(87) PCT Pub. No.: WO2018/088850
PCT Pub. Date: May 17, 2018

(65) Prior Publication Data
US 2023/0192875 A1    Jun. 22, 2023

(30) Foreign Application Priority Data
Nov. 11, 2016  (KR) ........................ 10-2016-0150624

(51) Int. Cl.
| | | |
|---|---|---|
| A61P 35/04 | (2006.01) | |
| C07K 16/28 | (2006.01) | |
| A61P 35/00 | (2006.01) | |
| A61K 39/00 | (2006.01) | |

(52) U.S. Cl.
CPC .......... *C07K 16/2878* (2013.01); *A61P 35/00* (2018.01); *A61K 2039/505* (2013.01); *C07K 2317/14* (2013.01); *C07K 2317/24* (2013.01); *C07K 2317/33* (2013.01); *C07K 2317/565* (2013.01); *C07K 2317/73* (2013.01); *C07K 2317/75* (2013.01); *C07K 2317/92* (2013.01)

(58) Field of Classification Search
CPC .............. A61P 35/04; A61K 2039/505; C07K 2317/565
USPC ................................ 424/133.1, 135.1, 136.1
See application file for complete search history.

(56) References Cited

U.S. PATENT DOCUMENTS

| | | |
|---|---|---|
| 5,801,227 A | 9/1998 | Fanslow, III et al. |
| 7,338,660 B2 | 3/2008 | Bedian et al. |
| 7,449,616 B2 | 11/2008 | Pons et al. |
| 8,496,937 B2 | 7/2013 | Schneider et al. |
| 8,980,257 B2 | 3/2015 | Kaneda et al. |
| 2005/0169923 A1 | 8/2005 | De Boer et al. |
| 2015/0309028 A1 | 10/2015 | Jordan |
| 2017/0088605 A1 | 3/2017 | Abend et al. |

FOREIGN PATENT DOCUMENTS

| | | | |
|---|---|---|---|
| AU | 2018202509 | * | 4/2018 |
| BG | 63489 B1 | * | 3/2002 |
| CA | 2243531 A1 | * | 7/1997 |
| KR | 10-2007-0012626 | | 1/2007 |
| KR | 10-2008-0030958 | | 4/2008 |
| KR | 10-2014-0009505 | | 1/2014 |
| NZ | 333602 | * | 3/1997 |
| NZ | 19970333602 | * | 6/2000 |
| WO | 2012/145673 | | 10/2012 |
| WO | 2016/069919 | | 5/2016 |

OTHER PUBLICATIONS

Juan C. Almagro et al., "Humanization of antibodies", Frontiers in Bioscience, vol. 13, pp. 1619-1633, 2008.
Im Muno Geno Tics, "Welcome! to IMGT/V-QUEST", http://www.imgt.org/IMGT_vquest/share/textes/, dicrectory release on Feb. 19, 2019.
Prof. Andrew C.R, "Antibodies", Martin's Group at UCL, last modified on Feb. 5, 2019, http://www.bioinf.org.uk/abs/.
GenBank: AHX81815.1, "immunoglobulin heavy chain variable region, partial [Mus musculus]", Apr. 2014.

* cited by examiner

*Primary Examiner* — Lynn A Bristol
(74) *Attorney, Agent, or Firm* — LEX IP MEISTER, PLLC

(57) ABSTRACT

The present invention relates to an anti-CD40 antibody binding specifically to CD40 and use thereof and, particularly, provides an anti-CD40 antibody or an antigen-binding fragment thereof, and a pharmaceutical composition comprising the same antibody or fragment as an effective ingredient for prevention and/or treatment of cancer, cancer metastasis, infection, and/or immune deficiency diseases.

18 Claims, 17 Drawing Sheets
Specification includes a Sequence Listing.

ANTIBODY BINDING SPECIFICALLY TO CD40 AND USE THEREOF

TECHNICAL FIELD

The present disclosure relates to an anti-CD40 antibody binding specifically to CD40 and a use thereof and, more particularly, to an anti-CD40 antibody or an antigen-binding fragment thereof and a composition comprising the same as an effective ingredient for prevention and/or treatment of cancer, cancer metastasis, infection, and/or immune deficiency diseases.

BACKGROUND ART

CD40 is a costimulatory protein molecule belonging to the tumor necrosis factor (TNF)-receptor superfamily found on antigen presenting cells (APC) including dendritic cells, B cells, and macrophages. The binding of the ligand CD154 (CD40L) on TH cells to CD40 activates antigen presenting cells. A variety of immune reactions including cytokine production, the upstream regulation of costimulatory molecules (e.g., CD86), and enhanced antigen presentation and B cell proliferation is accompanied by CD4-mediated APC activation. CD40 can also be expressed by endothelial cells, smooth muscle cells, fibroblasts, and epithelial cells.

Agonistic anti-CD40 antibodies constitute one of the most effective classes of these reagents. CD40 is a cell-surface member of the tumor necrosis factor superfamily expressed on antigen presenting cells (APC) such as dendrocytes, B cells and macrophages. Preclinical studies with anti-CD40 agonists suggest that triggering CD40 with crosslinking antibodies on antigen presenting cells (APC) can substitute for CD4 T cell help, normally provided via a CD40 ligand, and facilitate the activation as well as expansion of CD8 effector T cells. In addition, CD40-activated macrophages may also exert direct tumoricidal functions

PRIOR ART DOCUMENT

WO 2016/069919 A1 (May 6, 2016)

DETAILED DESCRIPTION OF THE INVENTION

Technical Problem

An embodiment provides an anti-CD40 antibody or an antigen-binding fragment thereof, which specifically recognizes CD40. The anti-CD40 antibody or the antigen-binding fragment thereof is characterized by recognizing a site different from the binding site between CD40 and the ligand thereof, CD40L. The anti-CD40 antibody or the antigen-binding fragment thereof is an agonist for CD40. In addition, the anti-CD40 antibody or the antigen-binding fragment thereof may not interfere with CD40/CD40L interaction by recognizing a site different from the binding site between CD40 and the ligand thereof, CD40L.

The anti-CD40 antibody or the antigen-binding fragment thereof may comprise:

heavy-chain complementarity determining regions (CDRs) or a heavy-chain variable region containing the heavy-chain complementarity determining regions (CDRs), the heavy-chain complementarity determining regions comprising: a polypeptide (CDR-H1) inclusive of the amino acid sequence of SEQ ID NO: 17 (GYGFTNYL) or SEQ ID NO: 33 (NYLIE); a polypeptide (CDR-H1) inclusive of the amino acid sequence of SEQ ID NO: 17 (GYGFTNYL) or SEQ ID NO: 33 (NYLIE); a polypeptide (CHR-H2) inclusive of the amino acid sequence of SEQ ID NO: 18 (INPGYGGV) or SEQ ID NO: 34 (VINPGYGGVNYNEKFKG); and a polypeptide (CHR-H3) inclusive of the amino acid sequence of SEQ ID NO: 19 (GGSGFAF); and light-chain complementarity-determining regions (CDRs) or a light-chain variable region containing the light-chain complementarity-determining regions, light-chain complementarity-determining regions comprising: a polypeptide (CDR-L1) inclusive of the amino acid sequence of SEQ ID NO: 20 (QDISNH) or SEQ ID NO: 35 (RASQDISNHLN); a polypeptide (CDR-L2) inclusive of the amino acid sequence of SEQ ID NO: 32 (STS(Xaa)n; wherein n means a number of any amino acid Xaa and may be an integer of 0 (Xaa is null) or 1 to 4; for example, a polypeptide having the amino acid sequence of SEQ ID NO: 21 (STS) or SEQ ID NO: 36 (STSRLHS)); and a polypeptide (CDR-L3) inclusive of the amino acid sequence of SEQ ID NO: 22 (QQGNTLP).

Another embodiment provides a hybridoma producing the anti-CD40 antibody.

Another embodiment provides a nucleic acid molecule coding for a heavy-chain complementarity-determining region, a heavy-chain variable region, or a heavy chain of an anti-CD40 antibody.

Another embodiment provides a nucleic acid coding for a light-chain complementarity-determining region, a light-chain variable region, or a light chain of an anti-CD40 antibody.

Another embodiment provides a recombinant vector carrying a nucleic acid molecule coding for a heavy-chain complementarity-determining region, a heavy-chain variable region, or a heavy chain of the anti-CD40 antibody and a nucleic acid molecule coding for a light-chain complementarity-determining region, a light-chain variable region, or a light chain of the anti-CD40 antibody together, or recombinant vectors carrying the nucleic acid molecules, respectively.

Another embodiment provides a recombinant cell anchoring the recombinant vector or the recombinant vectors thereat.

Another embodiment provides a pharmaceutical composition comprising an anti-CD40 antibody or an antigen-binding fragment thereof as an effective ingredient for preventing and/or treating a disease.

Another embodiment provides a method of preventing and/or treating a disease, the method comprising administering an anti-CD40 antibody or an antigen-binding fragment thereof to a subject in need of preventing and/or treating the disease.

Another embodiment provides a use of an anti-CD40 antibody or an antigen-binding fragment thereof in preventing and/or treating a disease or in preparing a composition for prevention and/or treatment of a disease.

The disease may be selected from cancer, cancer metastasis, infection, and immune deficiency disease.

Technical Solution

Provided herein are an anti-CD40 antibody specifically recognizing CD40 and a use thereof. The anti-CD40 antibody is characterized by recognizing a site different from the binding site between CD40 and its ligand CD40L and may exhibit agonistic activity for CD40. In addition, the anti-CD40 antibody or the antigen-binding fragment thereof may not interfere with CD40/CD40L interaction by recognizing a site different from the binding site between CD40 and its ligand CD40L. Herein, the expression "does not interfere with the CD40/CD40L interaction" is intended to mean not inhibiting the CD40/CD40L interaction at a significant level and to encompass some inhibition that does not incur a significant inhibitory effect.

CD40, which is a member of the tumor necrosis factor (TNF)-receptor superfamily, is a 45-50 kDa cell-surface antigen found on surfaces of normal and tumor human B cells, dendrocytes, monocytes, macrophages, CD8+ T cells, endothelial cells, mononuclear and epithelial cells, and many tumors (for example, solid tumors) including lung, breast, ovarian, bladder, and rectal cancers. CD40 is expressed in activated T cells, activated platelets, inflammatory vascular smooth muscle cells, synovium in rheumatoid arthritis, dermal fibroblasts, and non-lymphoma cells.

The CD40 acting as an antigen to the antibody provided herein may be derived from mammals, for example, human-derived CD40 (e.g., NCBI accession numbers NP_001241.1, NP_001289682.1, NP_690593.1, NP_001309351.1, and NP_001309350.1). There is an extracellular region among the five isoforms of human-derived CD40 and the anti-CD40 antibody provided in the present disclosure recognizes and/or binds the extracellular region.

Binding between CD40 and its homologous ligand CD40L (or CD154) incites B-cell proliferation and differentiation to plasma cells, antibody production, antibody isotype switching, and memory B-cell development. CD40L, which is a ligand for CD40, also known as CD154, is a 32-33 kDa transmembrane protein composed of two subunits 18 kDa and 31 kDa, respectively and is present in a soluble form, which is biologically active.

Interaction between CD40 and CD40L induces humoral and cell-mediated immune responses.

CD40 upregulates the above-mentioned ligand-receptor interaction to activate other antigen-presenting cells (APC) including monocytes, B cells and dendrocytes (DC). CD40 signaling on monocytes and DC enhances survival as well as secretion of cytokines (IL-1, IL-6, IL-8, IL-10, IL-12, TNF-α, and MIP-la). CD40 ligation to these APCs also induces upregulation of costimulatory molecules such as ICAM-1, LFA-3, CD80, and CD86. CD40 ligand activation is one of the signals that play a critical role in completely maturing DC to APC effective for driving T cell activation.

As used herein, the term "antibody" generically denotes a substance that is made with the stimulation of an antigen in the immune system or a protein that binds specifically to a certain antigen and has no particular limitations to kinds thereof. The antibodies may be those that are produced in a non-natural manner, for example, in a recombinant or synthetic manner. The antibodies may be animal antibodies (e.g., mouse antibodies, etc.), chimeric antibodies, humanized antibodies, or human antibodies. The antibodies may be monoclonal or polyclonal.

Unless stated otherwise, the antibody in the present disclosure may be understood to encompass an antigen-binding fragment thereof that possesses antigen binding capacity. The term "complementarity-determining regions (CDRs)", as used herein, means part of the variable region in an antibody, which confers binding specificity for an antigen. In this regard, the foregoing antigen-binding fragment of an antibody may be an antibody fragment comprising one or more of the complementarity-determining regions.

An embodiment of the present disclosure provides an anti-CD40 antibody or an antigen-binding fragment thereof that specifically recognize or binds to CD40.

The site on CD40 that is recognized or bound by the anti-CD40 antibody or the antigen-binding fragment thereof may be different from a site where CD40L interacts with or binds to CD40. The anti-CD40 antibody or the antigen-binding fragment thereof may have an agonist function for CD40. The anti-CD40 antibody or the antigen-binding fragment thereof may not interfere with CD40/CD40L interaction. In addition, the anti-CD40 antibody or the antigen-binding fragment thereof may have TAM (tumor associated macrophage) polarization and cancer cell apoptosis activity.

In a concrete embodiment, the anti-CD40 antibody or the antigen-binding fragment thereof may comprise, as the complementarity-determining region (CDR) in the heavy chain, a polypeptide (CDR-H1) comprising the amino acid sequence of SEQ ID NO: 17 (GYGFTNYL) or SEQ ID NO: 33 (NYLIE), a polypeptide (CDR-H2) comprising the amino acid sequence of SEQ ID NO: 18 (INPGYGGV) or SEQ ID NO: 34 (VINPGYGGVNYNEKFKG), and a polypeptide (CDR-H3) comprising the amino acid sequence of SEQ ID NO: 19 (GGSGFAF).

In addition, the anti-CD40 antibody or the antigen-binding fragment thereof may comprise, as the complementarity-determining region in the light chain, a polypeptide (CDR-L1) comprising the amino acid sequence of SEQ ID NO: 20 (QDISNH) or SEQ ID NO: 35 (RASQDISNHLN), polypeptide (CDR-L2) comprising the amino acid sequence of SEQ ID NO: 32 (STS(Xaa)n; wherein n means a number of any amino acid Xaa and may be an integer of 0 (Xaa is null) or 1 to 4; for example, SEQ ID NO: 21 (STS) or SEQ ID NO: 36 (STSRLHS)), and a polypeptide comprising the amino acid sequence (CDR-L3) of SEQ ID NO: 22 (QQGNTLP).

Therefore, the anti-CD40 antibody or the antigen-binding fragment thereof may comprise: a heavy chain complementarity-determining region or a heavy chain variable region inclusive of the heavy chain complementarity-determining region, the heavy chain complementarity-determining region comprising a polypeptide (CDR-H1) comprising the amino acid sequence of SEQ ID NO: 17 (GYGFTNYL) or SEQ ID NO: 33 (NYLIE), a polypeptide (CDR-H2) comprising the amino acid sequence of SEQ ID NO: 18 (INPGYGGV) or SEQ ID NO: 34 (VINPGYGGVNYNEKFKG), and a polypeptide (CDR-H3) comprising the amino acid sequence of SEQ ID NO: 19 (GGSGFAF); and a light chain complementarity-determining region or a light chain variable region inclusive of the light chain complementarity-determining region, the light chain complementarity-determining region comprising a polypeptide (CDR-L1) comprising the amino acid sequence of SEQ ID NO: 20 (QDISNH) or SEQ ID NO: 35 (RASQDISNHLN), a polypeptide (CDR-L2) comprising the amino acid sequence of SEQ ID NO: 32 (STS(Xaa)n; wherein n means a number of any amino acid Xaa and may be an integer of 0 (Xaa is null) or 1 to 4; for example, SEQ ID NO: 21 (STS) or SEQ ID NO: 36 (STSRLHS)), and a polypeptide (CDR-L3) comprising the amino acid sequence of SEQ ID NO: 22 (QQGNTLP).

The heavy-chain variable region may comprise the amino acid sequence of SEQ ID NO: 1, 23, 24, 25, 26, 27, or 28 (refer to Tables 1 and 6).

The light-chain variable region may comprise the amino acid sequence of SEQ ID NO: 3, 29, or 30 (refer to Tables 1 and 6).

When a medical treatment on humans is conducted therewith, animal-derived antibodies produced by immunizing non-immune animals with a desired antigen generally invoke an immune rejection response. In the interests of suppressing such immune rejection, a chimeric antibody has been developed. Chimeric antibodies are prepared using a genetic engineering technique in which constant regions of animal-derived antibodies causing an anti-isotype response are replaced by those of human antibodies. Although significantly improved in anti-isotype response when compared to their original animal-derived antibodies, chimeric antibodies still retain the potential risk of side effects of anti-idiotype responses because of the animal-derived amino acids incorporated into the variable region thereof. Humanized antibodies were developed to reduce such side effects. Humanized antibodies are produced by grafting complementarity determining regions (CDRs), critical to antigen binding, of variable regions of chimeric antibodies to a human antibody framework.

One important aspect of the CDR grafting process in producing humanized antibodies is to choose a human antibody optimized for accepting CDRs of animal-derived antibodies. To this end, utilization is made of antibody databases, crystal structure analysis, molecular modeling techniques, etc. However, even when CDRs of animal-derived antibodies are grafted to an optimized human antibody framework, there may be amino acids that are positioned in the framework of the animal-derived antibody and have an influence on antigen binding, which leads, in many cases, to a reduction in the antigen binding force. Hence, the production of humanized antibodies may require additional antibody engineering technology for recovering the antigen binding force.

According to one embodiment, the antibody may be an animal antibody (e.g., mouse antibody), a chimeric antibody (e.g., mouse-human chimeric antibody), or a humanized antibody.

The chimeric antibody may comprise:

a heavy chain comprising a heavy-chain variable region of a mouse antibody and a constant region of a human immunoglobulin (IgG (IgG1, IgG2, IgG3, IgG4, and the like), IgM, IgA, IgD, or IgE) (the C-terminus of the heavy-chain variable region is linked to the N-terminus of the constant region); and a light chain comprising a light-chain variable region and a kappa (κ)- or lambda (λ)-type constant region of a mouse antibody (the C terminus of the light-chain variable region is linked to the N terminus of the constant region).

In an embodiment, the chimeric antibody may comprise, as a heavy chain, a heavy-chain variable region of a mouse antibody and a constant region of human IgG, for example, human IgG1, human IgG2, human IgG3, or human IgG4. In an embodiment, the chimeric antibody may comprise, as a heavy chain, a heavy-chain variable region of a mouse antibody and a constant region of human IgG4.

The humanized antibody may comprise:

a heavy chain comprising a complementarity-determining region (CDR) of a mouse antibody and a framework (a variable domain region exclusive of CDR) and a heavy chain of a human immunoglobulin (IgG (IgG1, IgG2, IgG3, IgG4, and the like), IgM, IgA, IgD, or IgE); and a light chain comprising a light-chain CDR and a kappa (κ)- or lambda (λ)-type framework and constant region of a mouse antibody.

In an embodiment, the humanized antibody may comprise, as a heavy chain, a heavy-chain CDR of a mouse antibody and a framework and constant region of a human IgG, for example, human IgG1, human IgG2, human IgG3, or human IgG4. In an embodiment, the humanized antibody may comprise, as a heavy chain, a heavy-chain CDR of a mouse antibody and a framework and constant region of a human IgG4.

An intact antibody has a structure composed of two full-length light chains and two full-length heavy chains where each light chain is linked to the heavy chain by disulfide bonds. A constant region is present in each of the heavy and the light chains. The heavy chain constant region is of a gamma (γ), mu (μ), alpha (α), delta (δ), or epsilon (ε) type, which can be further subclassified into gamma 1 (γ1), gamma 2 (γ2), gamma 3 (γ3), gamma 4 (γ4), alpha 1 (α1), or alpha 2 (α2). The light chain constant region is of either a kappa (κ) or lambda (λ) type.

As used herein, the term "heavy chain" is intended to encompass a full-length heavy chain composed of a variable region VH comprising an amino acid sequence sufficient to confer specificity for an antigen on the antibody, three constant region domains CH1, CH2, and CH3, a hinge, and a fragment of the full-length heavy chain. The term "light chain" refers to a full-length light chain composed of a variable region VL comprising an amino acid sequence sufficient to confer specificity for an antigen on the antibody, and a constant region CL, or a fragment of the full-length light chain.

The term "CDR (complementarity determining region)" denotes an amino acid sequence which resides in the heavy chain and the light chain hypervariable regions of an immunoglobulin. Each heavy and light chain has three CDRs (CDRH1, CDRH2, CDRH3, and CDRL1, CDRL2, CDRL3). The CDRs provide contact residues that play a major role in the binding of antibodies to antigens or epitopes. As used herein, the term "specifically binding" or "specifically recognizing" has the same meaning as is well known to one of ordinary skill in the art, and indicates that an antibody and an antigen specifically interact with each other to induce an immunological activity.

The term "antigen-binding fragment" refers to a fragment of the whole immunoglobulin structure which possesses a part of a polypeptide responsible for antigen binding. Examples of the antigen-binding fragment useful in the present disclosure comprise scFv, (scFv)2, Fab, Fab' and F(ab')2, but are not limited thereto.

Of the antigen-binding fragment, Fab is composed of one variable and one constant domain from the light chain, and one variable and the first constant (CH1) domain from the heavy chain, retaining one antigen-binding site.

A Fab' fragment is different from Fab in that the Fab' further comprises a hinge region having at least one cysteine residue at the C-terminus of the heavy chain CH1 domain.

A F(ab')2 antibody forms as two Fab' fragments are joined by a disulfide bond between the cysteine residues of the hinge region. A Fv fragment is a minimal antibody fragment composed only of variable domains from the heavy chain and the light chain. Recombinant techniques for producing the Fv are well known in the art.

In a two-chain Fv fragment, the heavy chain variable domains are associated with the light chain variable domains via a non-covalent bond. A single-chain Fv fragment has a structure in which a heavy chain variable domain and a light chain variable domain are covalently joined to each other via a covalent bond or directly at the C-terminus, so that it can form a dimer as in a two-chain Fv fragment.

The antigen-binding fragment may be obtained using a protease (for example, a whole antibody can be digested with papain to obtain Fab fragments, or can be digested with pepsin to obtain F(ab')2 fragments), or may be prepared by a genetic recombinant technique.

The term "hinge region" refers to a region that is located between CH1 and CH2 regions in the heavy chains of an antibody, presenting flexibility to the antigen binding site in then antibody.

The anti-CD40 antibody may be a monoclonal antibody. Monoclonal antibodies may be prepared using a method well known in the art, for example, a phase display technique. Alternatively, the anti-CD40 antibody may be prepared as a mouse-derived monoclonal antibody by any conventional method.

Meanwhile, individual monoclonal antibodies can be screened on the basis of their CD40 binding capacity by using a typical ELISA (Enzyme-Linked ImmunoSorbent Assay) format. They may be analyzed for inhibitory activity by using a functional assay, such as competitive ELISA for examining molecular interactions between components within a complex, and cell-based assay. Then, the monoclonal antibody members selected based on potent inhibitory activity may be tested for their respective affinities to CD40 (Kd values).

Finally selected antibodies are composed of human immunoglobulin antibodies except for antigen binding portions and may be prepared as humanized antibodies. Preparation methods of humanized antibodies are well known in the art (Almagro, J. C. and Fransson, J., "Humanization of antibodies," Frontiers in Bioscience, 13(2008), 1619-1633).

Another aspect provides a hybridoma producing the anti-CD40 antibody. In an embodiment, the hybridoma may be one deposited with accession number KCLRF-BP-00381.

Another aspect provides an anti-CD40 antibody produced by the hybridoma, or an antigen-binding fragment thereof.

Another aspect provides an anti-CD40 antibody or an antigen-binding fragment thereof, the anti-CD40 antibody comprising a heavy-chain complementarity-determining region (CDR-H1, CDR-H2, CDR-H3, or a combination thereof) or a light-chain complementarity-determining region (CDR-L1, CDR-L2, CDR-L3, or a combination thereof) in the anti-CD40 antibody produced by the hybridoma, or a combination thereof; or a heavy-chain variable region or a light-chain variable region in the anti-CD40 antibody produced by the hybridoma, or a combination thereof. In this regard, the complementarity-determining regions may be determined by all typical methods, for example, IMGT definition or Cabat definition, but not limited thereto.

Another aspect provides a pharmaceutical composition comprising the anti-CD40 antibody or the antigen-binding fragment thereof as an effective ingredient for preventing and/or treating disease. Another aspect provides a use of the anti-CD40 antibody or the antigen-binding fragment thereof in preventing and/or treating a disease or in preparing a composition for treatment and/or prevention of disease. Another aspect provides a method for preventing and/or treating a disease, the method comprising administering the anti-CD40 antibody or the antigen-binding fragment thereof in a therapeutically effective amount to a subject in need thereof. The method for preventing and/or treating a disease may further comprise identifying the subject in need of the prevention and/or treatment of the disease prior to the administration step. The disease may be selected from cancer, cancer metastasis, infection, and immune deficiency diseases.

The pharmaceutical composition may further comprise a pharmaceutically acceptable carrier. The pharmaceutically acceptable carrier may be one that is typically used for formulating a drug. Examples of the pharmaceutically acceptable carrier comprise lactose, dextrose, sucrose, sorbitol, mannitol, starch, gum acacia, calcium phosphate, alginate, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. Also, the pharmaceutical composition may further comprise a typical additive selected from the group consisting of a diluent, an excipient, a lubricant, a humectant, a sweetener, a flavor enhancer, an emulsifier, a suspending agent, a preservative, and a combination thereof.

An effective amount of the pharmaceutical composition, or the antibody or the antigen-binding fragment thereof may be administered orally or parenterally. For parenteral administration, selection may be made of an intravenous, subcutaneous, intramuscular, intraperitoneal, intradermal, intranasal, intrapulmonary, intrarectal, or perilesional route. For oral administration, however, the pharmaceutical composition may be coated or formulated to protect the active ingredient from being degraded in the stomach because proteins or peptides are digested by pepsin. In addition, the administration may be performed with the aid of an instrument adapted for delivering the pharmaceutical composition to target cells.

The content of the anti-CD40 antibody or the antigen-binding fragment thereof in the pharmaceutical composition or the administration amount of the anti-CD40 antibody or the antigen-binding fragment thereof may be determined in consideration of various factors comprising the type of formulation, the patent's age, weight, and sex, the severity of the disorder being treated, diet, the time of administration, the interval of administration, the route of administration, the rate of excretion, and sensitivity. For example, the daily dose of the anti-CD40 antibody or the antigen-binding fragment thereof may be on the order of 0.001 to 1000 mg/kg, particularly on the order of 0.01 to 100 mg/kg, more particularly on the order of 0.1 to 50 mg/kg, and far more particularly on the order of 0.1 to 20 mg/kg, but is not limited thereto. A daily dose may be formulated into a unit dose form or distributed into separate dose forms or may be comprised within a multiple dose package.

The pharmaceutical composition may be administered in combination with a different drug such as an anticancer agent. In this regard, the dose and administration route of the pharmaceutical composition, and kinds of the different drug may be determined appropriately depending on states of patients.

The pharmaceutical composition may be formulated into solutions in oil or aqueous media, suspensions, syrup, emulsions, elixirs, powders, granules, tablets, or capsules, and in this context, a dispersant or a stabilizer may be further employed.

The subject to which the pharmaceutical composition is to be administered may be a mammal, examples of which comprise primates such as humans or monkeys, and rodents such as mice and rats.

The cancer may be a solid cancer or a blood cancer. The cancer may be selected from the group consisting of squamous cell carcinoma, small-cell lung cancer, non-small-cell lung cancer, adrenocarcinoma of lung, squamous cell carcinoma of lung, peritoneal cancer, skin cancer, skin or intraocular melanoma, rectal cancer, perianal cancer, esophagus cancer, small intestine cancer, endocrine gland cancer, parathyroid cancer, adrenal cancer, soft-tissue sarcoma, urethral cancer, leukemia (e.g., chronic or acute leukemia), lymphoma, hepatoma, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, and a combination thereof, but is not limited thereto. The cancer may be a primary cancer or a metastatic cancer.

As used herein, the term "treatment of cancer" is intended to encompass all anticancer actions by which cancer symptoms are prevented from aggravation, alleviated, or reversed toward a better condition, such as inhibiting cancer cell proliferation, killing cancer cells, suppressing cancer metastasis, etc., or by which cancer is eliminated partially or entirely.

The specific binding of the anti-CD40 antibody or the antigen-binding fragment thereof to CD40 can be utilized to detect or identify CD40. Accordingly, another aspect of the present disclosure provides a composition for detection of CD40, the composition comprising the anti-CD40 antibody or the antigen-binding fragment thereof. Another aspect provides a method for detection of CD40, the method comprising the steps of: treating a biological sample with the anti-CD40 antibody or the antigen-binding fragment thereof; and examining whether an antigen-antibody reaction has occurred or not. In the detection method, an antigen-antibody reaction, if occurring, might lead to determining (deciding) the presence of CD40 in the biological sample. Therefore, the detection method may further comprise determining the presence of CD40 in the biological sample when the antigen-antibody reaction is detected after the identifying step. The biological sample may be selected from cells, tissues, or body fluids, obtained (isolated) from a human (e.g., a cancer patient), or from a culture thereof.

The examination of an antigen-antibody reaction may be carried out using a method well known in the art, for example, on the basis of an enzyme reaction, fluorescence, luminescence, and/or radiation. Examples of the method useful for examining the antigen-antibody reaction of the biological sample may comprise immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), Western blotting, and microarray, but are not limited thereto.

Another aspect provides a polypeptide molecule comprising a heavy-chain complementarity-determining region, a light-chain complementarity-determining region, or a combination thereof; or a heavy-chain variable region, a light-chain variable region, or a combination thereof in the anti-CD40 antibody described above.

The polypeptide may be used as a precursor in constructing an antibody or may be comprised as a constituent in a protein scaffold (e.g., peptibody) having a structure analogous to that of an antibody, a bispecific antibody, and a multispecific antibody.

Another aspect provides a nucleic acid coding for a heavy-chain complementarity-determining region, a heavy-chain variable region, or a heavy chain in the anti-CD40 antibody.

Another aspect provides a nucleic acid molecule coding for a light-chain complementarity-determining region, a light-chain variable region, or a light chain in the anti-CD40 antibody.

Another aspect provides a recombinant vector carrying a nucleic acid molecule coding for a heavy-chain complementarity-determining region, a heavy-chain variable region, or a heavy chain of the anti-CD40 antibody and a nucleic acid molecule coding for a light-chain complementarity-determining region, a light-chain variable region, or a light chain of the anti-CD40 antibody together, or recombinant vectors carrying the nucleic acid molecules respectively.

Another aspect provides a recombinant cell harboring the recombinant vector thereat.

The term "vector" refers to a means for expressing a target gene in a host cell, as exemplified by a plasmid vector, a cosmid vector, and a viral vector such as a bacteriophage vector, an adenovirus vector, a retrovirus vector, and an adeno-related virus vector. The recombinant vector may be constructed from plasmids frequently used in the art (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19), phages (for example, λgt4λB, λ-Charon, λΔz1, and M13) or viruses (for example, SV40, etc.) by manipulation.

In the recombinant vector, the nucleic acid molecule may be operatively linked to a promoter. The term "operatively linked" is intended to pertain to a functional linkage between a nucleotide sequence of interest and an expression regulatory sequence (for example, a promoter sequence). When being "operatively linked, the regulatory element can control the transcription and/or translated of the nucleotide of interest.

The recombinant vector may be constructed typically as a cloning vector or an expression vector. For recombinant expression vectors, a vector typically available for expressing a foreign protein in plant, animal, or microorganism cells may be employed. Various methods well known in the art may be used for the construction of recombinant vectors.

For use in hosts, such as prokaryotic or eukaryotic cells, the recombinant vector may be constructed appropriately. For example, when a vector is constructed as an expression vector for us in a prokaryotic host, the vector typically comprises a strong promoter for transcription (e.g., a pLκλ promoter, a CMV promoter, a trp promoter, a lac promoter, a tac promoter, a T7 promoter, etc.), a ribosomal binding site for initiating translation, and transcriptional/translational termination sites. On the other hand, an expression vector for use in a eukaryotic host comprises an origin of replication operable in a eukaryotic cell, such as an f1 origin of replication, an SV40 origin of replication, a pMB1 origin of replication, an adeno origin of replication, an AAV origin of replication, and a BBV origin of replication, but is not limited thereto. In addition, the expression vector typically comprises a promoter derived from genomes of mammalian cells (for example, metallothionein promoter) or from mammalian viruses (for example, adenovirus late promoter, vaccinia virus 7.5K promoter, SV40 promoter, cytomegalovirus promoter, and tk promoter of HSV), and a polyadenylation sequence as a transcription termination sequence.

Another aspect provides a recombinant cell harboring the recombinant vector thereat.

The recombinant cell may be prepared by introducing the recombinant vector into a suitable host cell. So long as it allows for the sequential cloning and expression of the recombinant vector in a stable manner, any host cell known in the art may be employed in the present disclosure. Examples of the prokaryotic host cell available for the present disclosure comprise *E. coli* JM109, *E. coli* BL21, *E. coli* RR1, *E. coli* LE392, *E. coli* B, *E. coli* X 1776, *E. coli* W3110, *Bacillus* spp. such as *Bacillus subtilis* and *Bacillus thuringiensis*, and enterobacteriaceae strains such as *Salmonella typhimurium*, *Serratia marcescens* and various *Pseudomonas* species. Eukaryotic host cells to be transformed may be, but not limited to, *Saccharomyce cerevisiae*, insect cells, and animal cells, such as Sp2/0, CHO (Chinese hamster ovary) K1, CHO DG44, PER.C6, W138, BHK, COS-7, 293, HepG2, Huh7, 3T3, RIN, and MDCK.

Using a method well known in the art, the nucleic acid molecule or a recombinant vector carrying the same may be introduced (incorporated) into a host cell. This transformation may be carried out using a $CaCl_2$) or electroporation method when the host cell is prokaryotic. For eukaryotic host cells, the genetic introduction may be achieved using, but not limited to, microinjection, calcium phosphate precipitation, electroporation, liposome-mediated transfection, or particle bombardment.

To select a transformed host cell, advantage may be taken of the phonotype attributed to a selection marker according to a method known in the art. For example, when the selection marker is a gene resistant to a certain antibiotic, the host cells may be grown in the present of the antibiotic in a medium to select a transformant of interest.

Another aspect provides a method for producing an anti-CD40 antibody, the method comprising a step of expressing the nucleic acid molecule or a recombinant vector carrying the same in a host cell. The production method may comprise culturing a recombinant cell harboring the recombinant vector thereat, and optionally isolating and/or purifying the antibody from the culture medium.

Advantageous Effects

The present disclosure provides an anti-CD40 antibody that binds specifically to CD40, has an agonistic function for CD40, and does not interfere with CD40/CD40L interaction, thereby allowing more effective treatment of cancer.

MODE FOR CARRYING OUT THE INVENTION

Figure 1:
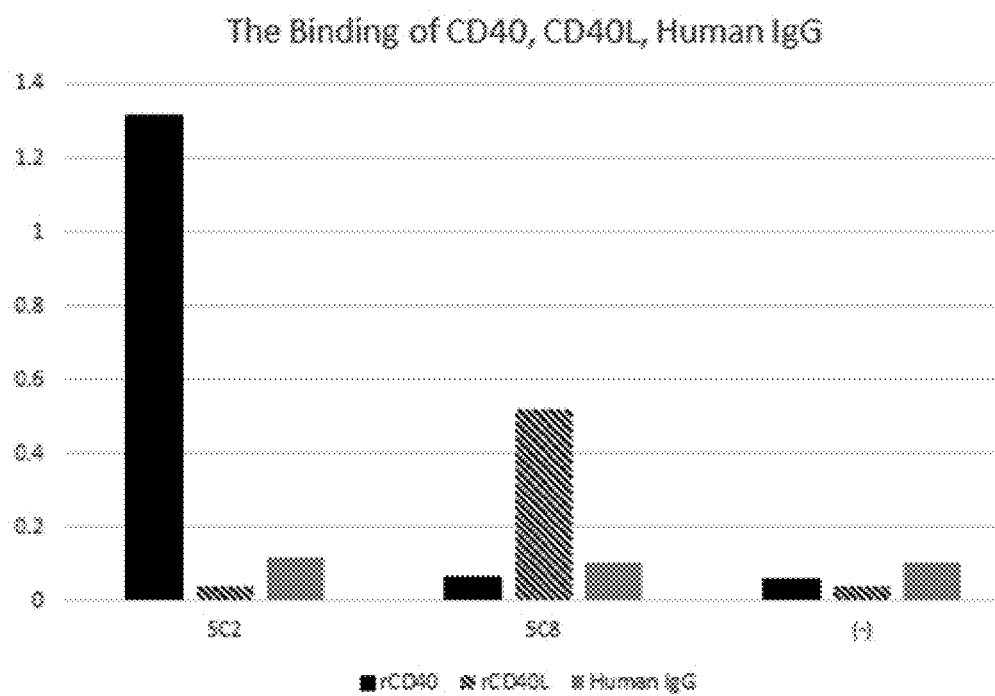
FIG. 1 is a graph showing binding affinity of anti-CD40 monoclonal antibody 5C2 to CD40 (rCD40: recombinant human CD40; rCD40L: recombinant antigen human CD40L).

Hereinafter, the present invention will be described in detail with reference to examples. These examples are only for illustrating the present invention more specifically, and it will be apparent to those skilled in the art that the scope of the present invention is not limited by these examples.

Example 1: Production of Anti-CD40 Antibody 1-1. Mouse Antibody Preparation
1-1-1. Preparation of Monoclonal Antibody-Producing Cell Splenocytes from a Balb/c mouse injected with a human recombinant protein CD40 antigen were fused to the myeloma cell line X63-Ag8.653 (ATCC®, PTA-8431) from an 8-azaguanine-resistant mouse. To this end, Balb/c mice were each injected with 100 µg of the human CD40 recombinant antigen every two weeks for six weeks to induce an immune reaction. On day 3 after the final inoculation, splenocytes were isolated and suspended. According to Koeler and Milstein's method (Koeler & Milstein 1975), $10^8$ splenocytes and $10^7$ myeloma cells were fused to each other using 50% polyethylene glycol 400 in DMEM (Dulbeco's modified Eagle's medium). The fused cells were washed and then resuspended in a DMEM medium supplemented with 20% fetal bovine serum, 100 µM hypoxanthine, 0.44 µM aminopterin, and 16 µM thymidine (HAT culture medium). The cells ere plated into 96-well plates and cultured at 37° C. in an incubator supplied with 5% $CO_2$.

When colonies were observed two weeks later, the supernatant was taken and analyzed using ELISA (Enzyme-Linked ImmunoSorbent Assay) to examine whether to bind to CD40.

For a positive group, selection was made of wells in which $10^5$ or more cells per well were formed in a single moiety. After being taken from the wells where colonies were formed with the supernatant measured to have a high antibody titer, cells were subcloned according to limiting dilution assay to obtain monoclonal cells having a high antibody titer. A supernatant was taken from the monoclonal cell culture and stored until the subsequent experiment.

1-1-2. Selection of Monoclonal Cell Producing Antibody to Human CD40

Human recombinant CD40 (R&D systems, Cat. No.: P25942) was plated in an amount of 100.0 ng per well into a MaxiSorp ELISA plate and reacted at 37° C. for one hour for antibody coating, followed by blocking by incubation with 200 µL of 1× blocking solution (Sigma) per well at 37° C. for one hour.

The monoclonal cell culture was added at a density of 100 µL/well, incubated at 37° C. for one hour, and washed three times with phosphate buffered saline before treatment with the secondary antibody goat anti-mouse IgG-HRP. Incubation at 37° C. for 30 minutes was followed by three rounds of washing with phosphate buffered saline. Then, TMB Single Solution (Life Technologies, Cat. No: 002023) was added in an amount of 100 µl per well and incubated at room temperature for 5-10 min in a dark place. Color development was stopped with 100 µL of 1.0 N sulfuric acid and absorbance at 450 nm was measured.

As a result, the monoclonal cell line 5C2 that produced an antibody reacting specifically with the recombinant antigen human CD40 could be selected. The cell line thus obtained was deposited Nov. 2, 2016, with the Korean Cell Line Research Foundation (KCLRF), located in Yongon-Dong, Chongno-Gu, Seoul, under accession number KCLRF-BP-00381.

1-1-3. Production of Monoclonal Antibody from Selected Monoclonal Cell Line

The established cell line 5C2 was cultured in a 10% fetal bovine serum-supplemented RPMI medium at 37° C. for two weeks under a 5% $CO_2$ condition.

After being sterilized by filtration, the cell line culture was loaded into HiTrap Protein G HP column (GE Healthcare, Cat. No.: 17-0405-03) equilibrated with Protein G equilibration buffer (20 mM phosphate, pH7.4), washed by flowing the equilibration buffer through the column, and recovered with an elution buffer (20 mM Citric acid pH3.0). The recovered antibody was named 5C2 (mouse antibody) and dialyzed against phosphate buffered saline to exchange the buffer for use in subsequent tests.

1-1-4. Assay for Specificity of Monoclonal Anti-CD40 Antibody

For assay for the specificity of the anti-CD40 5C2 antibody (mouse antibody), reactivity against a recombinant antibody human CD40 (rCD40; R&D systems, Cat. No.: P25942), a recombinant antigen human CD40L (Recombinant Human sCD40 Ligand; Peprotech, Cat. No.: 310-02; amino acid sequence: MQKGDQNPQI AAHVISEASS KTTSVLQWAE KGYYTMSNNL VTLENGKQLT VKRQGLYYIY AQVTFCSNRE ASSQAPFIAS LWLKSPGRFE RILLRAANTH SSAKPCGQQS IHLGGVFELQ PGASVFVNVT DPSQVSHGTG FTSFGLLKL (SEQ ID NO: 31)), and a human IgG (Dinona) was analyzed using ELISA. The three antigens were each diluted at a density of 1.0 μg/mL in phosphate buffered saline and the dilution was plated at 100 μL/well into microplates and incubated at 37° C. for one hour to coat the plates therewith. Then, a 1× blocking solution (Sigma) was added in an amount of 200 μL per well and incubated at 37° C. for one hour to block the antigens.

Anti-CD40 antibody 5C2 and anti-CD40L 5C8 (ATCC®, ATCC HB-10916; positive control) were each diluted to a density of 1.0 μg/mL in phosphate buffered saline, and the dilutions were added in an volume of 100 μL per well and incubated at 37° C. for one hour, washed three times with phosphate buffered saline, and treated with the secondary antibody goat anti-mouse IgG-HRP. After 30 min of incubation at 37° C., the wells were washed three times with phosphate buffered saline, added with TMB Single Solution (Life Technologies, Cat. No: 002023) in an amount 100 μL per well, and incubated at room temperature for 5-10 min in a dark place. The color development was stopped with 100 μL of 1.0 N sulfuric acid and absorbance at 450 nm was measured.

The results obtained are depicted in FIG. 1. In FIG. 1, the y axis represents absorbance. As shown in FIG. 1, 5C2 antibody was identified to bind specifically to the human CD40 antigen because of no cross reactivity for CD40L or human IgG.

1-2. Preparation of Chimeric Antibody

On the basis of the amino acid sequence of the produced anti-CD40 mouse antibody 5C2, an anti-CD40 chimeric antibody was prepared.

1-2-1. Plasmid Construction

For use in expressing an anti-CD40 chimeric antibody, a heavy-chain expressing plasmid and a light-chain expressing plasmid were constructed, separately. Both the heavy-chain and light-chain expressing plasmids were based on the pcDNA3.4 vector (Invitrogen).

Heavy- and light-chain variable region-encoding cDNA for antibody expression were cloned using Ig-Primer sets (Novagen), inserted into pCR2.1 vector (Invitrogen, Cat. No.: K200001), and identified by sequencing. A mouse antibody gene was identified with the aid of the IMGT site (www.imgt.org).

The amino acid sequences of heavy- and light-chain variable regions in the mouse 5C2 monoclonal antibody and the nucleotide sequence of the coding gene therefor are as follows.

TABLE 1

Amino acid sequence of Variable Region in Anti-CD40 Mouse 5C2 Monoclonal Antibody

| | Amino acid sequence | Coding gene (DNA) sequence |
|---|---|---|
| Heavy-chain variable region sequence (VH) | QVQMLQSGTELVRPGT SVKVSCKAS<u>GYGFTNY</u> LIEWVKQRPGQGLEWIG VIN<u>PGYGGVNYNEKFK</u> GKAILTADKSSSTAYMH LTSLTSDDSAVYFCARG <u>GSGFAFWGQGTLVTVS</u> T (SEQ ID NO: 1) | CAGGTACAGATGCTGCAGAGCGGAACTGAACTG GTTAGACCTGGTACTAGCGTTAAGGTCAGCTGTA AGGCTAGCGGATACGGTTTCACCAACTACCTGAT CGAATGGGTCAAGCAGAGGCCAGGACAAGGTTT GGAGTGGATTGGAGTGATTAACCCCGGGTATGG GGGCGTGAATTACAATGAGAAGTTTAAAGGCAA AGCCATACTGACCGCAGACAAATCAAGTAGTAC CGCCTATATGCACCTGACATCTTTGACATCTGAC GATTCTGCCGTGTATTTTTGCGCCCGGGGCGGGA GTGGCTTTGCTTTTTGGGGCCAGGGCACACTTGT GACTGTGTCTACA (SEQ ID NO: 2) |
| Light-chain variable region sequence (VL) | DIQMTQTTSSLSASLGQ RVTISCRAS<u>QDISNHLN</u> WYQQKPNGTVRLLIS<u>ST SRLHSGVPSRFSGSGSG</u> TDYSLTISNLEQEDIATY FC<u>QQGNTLPWT</u>FGGGT KLEIK (SEQ ID NO: 3) | GACATCCAAATGACCCAAACCACCTCCTCACTTT CCGCATCTCTTGGACAAAGAGTCACCATCTCCTG FAGGGCAAGTCAAGACATCTCCAACCACCTCAAC FGGTACCAGCAGAAGCCAAACGGAACTGTTAGG FTGTTGATCTCCAGCACCTCACGTTTGCACTCAG GAGTACCATCACGATTCAGCGGTAGTGGTTCTGG FACAGATTACAGCTTGACCATTAGCAACCTGGAG CAGGAGGATATTGCTACCTACTTCTGCCAGCAGG GCAATACCCTGCCTTGGACATTTGGGGGGGGCAC AAAACTGGAAATTAAG (SEQ ID NO: 4) |

(CDR1, CDR2, and CDR3 (according to the IMGT definition) are sequentially underlined)

In order to allow the variable region-encoding cDNAs and constant region-encoding cDNA to be expresses as sequential amino acid sequences in antibodies, respective gene fragments in which the cloned variable region-encoding nucleotide sequences were linked to nucleotide sequences coding for the constant region (heavy chain) of known human IgG1, human IgG2, and human IgG4 (S228P, serine at position 228 was substituted with proline) and the kappa constant region (light chain) were synthesized (Bioneer). As such, the synthesized heavy- and light-chain expressing genes were digested with restriction enzymes Xho I and EcoR1. The heavy chain and light chain gene fragments thus obtained were ligated to respective pcDNA3.4 vectors to construct antibody-expressing vectors for three heavy chains and one light chain. The amino acid sequences of the heavy and light chains in the three chimeric antibodies thus constructed and nucleotide sequences coding therefor are summarized in Table 2, below:

TABLE 2

Amino acid sequences of heavy and light chains in three chimeric antibodies and nucleotide sequence coding therefor
(bolds represent variable regions)

| | Amino acid sequence | Nucleotide sequence (cDNA) |
|---|---|---|
| Heavy chain of chimeric IgG1 Ab (comprising human IgG1 Constant region) | QVQMLQSGTELVRP GTSVKVSCKASGYGF TNYLIEWVKQRPGQ GLEWIGVINPGYGGV NYNEKFKGKAILTAD KSSSTAYMHLTSLTS DDSAVYFCARGGSGF AFWGQGTLVTVSTA STKGPSVFPLAPSSKST SGGTAALGCLVKDYF PEPVTVSWNSGALTSG VHTFPAVLQSSGLYSL SSVVTVPSSSLGTQTYI CNVNHKPSNTKVDKK VEPKSCDKTHTCPPCP APELLGGPSVFLFPPKP KDTLMISRTPEVTCVV VDVSHEDPEVKFNWY VDGVEVHNAKTKPRE EQYNSTYRVVSVLTV LHQDWLNGKEYKCK VSNKALPAPIEKTISKA KGQPREPQVYTLPPSR DELTKNQVSLTCLVK GFYPSDIAVEWESNGQ PENNYKTTPPVLDSDG SFFLYSKLTVDKSRWQ QGNVFSCSVMHEALH NHYTQKSLSLSPGK (SEQ ID NO: 5) | CAGGTACAGATGCTGCAGAGCGGAACTGAACTG GTTAGACCTGGTACTAGCGTTAAGGTCAGCTGTA AGGCTAGCGGATACGGTTTCACCAACTACCTGAT CGAATGGGTCAAGCAGAGGCCAGGACAAGGTTT GGAGTGGATTGGAGTGATTAACCCCGGGTATGG GGGCGTGAATTACAATGAGAAGTTTAAAGGCAA AGCCATACTGACCGCAGACAAATCAAGTAGTAC CGCCTATATGCACCTGACATCTTTGACATCTGAC GATTCTGCCGTGTATTTTTGCGCCCGGGGCGGG AGTGGCTTTGCTTTTTGGGGCCAGGGCACACTT GTGACTGTGTCTACAGCTTCAACTAAGGGACCAA GCGTATTCCCACTTGCTCCATCTAGCAAGAGCACTA GCGGAGGAACAGCTGCTTTGGGGTGTTTGGTAAAG GATTACTTTCCCGAACCTGTTACCGTGAGCTGGAAC AGCGGGGCTTTGACAAGTGGCGTTCATACATTTCCT GCCGTTTTGCAAAGCAGCGGCTTGTATAGCTTGAGC TCTGTTGTTACCGTTCCAAGCTCATCTCTGGGCACA CAAACATACATCTGCAACGTGAACCACAAGCCCTC AAACACCAAGGTGGACAAGAAGGTGGAGCCAAAG TCTTGCGACAAGACCCACACCTGTCCACCTTGTCCA GCCCCTGAACTCCTGGGGGGCCCTTCAGTTTTTCTC TTTCCTCCTAAACCTAAAGATACACTCATGATCAGT CGGACCCCTGAAGTTACCTGTGTGGTGGTCGATGTG TCTCATGAAGATCCTGAAGTCAAGTTTAACTGGTAT GTGGACGGCGTGGAGGTGCATAATGCCAAGACCAA GCCTCGGGAGGAGCAATATAATTCTACCTATCGCGT CGTCTCTGTCCTCACCGTCCTGCATCAGGACTGGCT GAATGGCAAAGAGTATAAGTGCAAAGTCAGTAACA AAGCCCTCCCCGCCCCCATAGAGAAAACCATTAGT AAAGCCAAAGGGCAGCCCCGCGAGCCCCAGGTCTA TACACTGCCCCCCAGTAGAGACGAGCTGACAAAGA ATCAGGTGTCTCTGACATGCCTGGTGAAAGGCTTTT ATCCCTCTGACATTGCCGTCGAGTGGGAGTCTAATG GGCAGCCCGAGAATAATTATAAGACAACACCCCCC GTGCTGGACAGTGACGGCTCATTTTTCCTGTATTCA AAACTGACAGTGGACAAAAGTCGGTGGCAGCAGGG GAATGTGTTTTCATGCAGTGTCATGCACGAGGCCCT CCACAATCACTATACCCAGAAATCTCTGAGTCTCTC TCCTGGGAAATGA (SEQ ID NO: 6) |
| Heavy chain of IgG2 chimeric Ab (comprising human IgG2 constant region) | QVQMLQSGTELVRP GTSVKVSCKASGYGF TNYLIEWVKQRPGQ GLEWIGVINPGYGGV NYNEKFKGKAILTAD KSSSTAYMHLTSLTS DDSAVYFCARGGSGF AFWGQGTLVTVSTA STKGPSVFPLAPCSRST SESTAALGCLVKDYFP EPVTVSWNSGALTSG VHTFPAVLQSSGLYSL SSVVTVPSSNFGTQTY TCNVDHKPSNTKVDK TVERKCCVECPPCPAP PVAGPSVFLFPPKPKD TLMISRTPEVTCVVVD VSHEDPEVQFNWYVD GVEVHNAKTKPREEQ FNSTFRVVSVLTVVHQ DWLNGKEYKCKVSN KGLPAPIEKTISKTKGQ PREPQVYTLPPSREEM TKNQVSLTCLVKGFYP SDIAVEWESNGQPENN YKTTPPMLDSDGSFFL YSKLTVDKSRWQQGN VFSCSVMHEALHNHY TQKSLSLSPGK (SEQ | CAGGTACAGATGCTGCAGAGCGGAACTGAACTG GTTAGACCTGGTACTAGCGTTAAGGTCAGCTGTA AGGCTAGCGGATACGGTTTCACCAACTACCTGAT CGAATGGGTCAAGCAGAGGCCAGGACAAGGTTT GGAGTGGATTGGAGTGATTAACCCCGGGTATGG GGGCGTGAATTACAATGAGAAGTTTAAAGGCAA AGCCATACTGACCGCAGACAAATCAAGTAGTAC CGCCTATATGCACCTGACATCTTTGACATCTGAC GATTCTGCCGTGTATTTTTGCGCCCGGGGCGGG AGTGGCTTTGCTTTTTGGGGCCAGGGCACACTT GTGACTGTGTCTACAGCTTCCACCAAGGGCCCATC CGTGTTCCCTCTGGCCCCATGTTCTAGGTCTACATCT GAGAGCACCGCCGCCCTCGGCTGTCTGGTGAAGGA TTATTTCCCCGAGCCCGTGACCGTGTCTTGGAACAG CGGAGCCCTGACTAGCGGAGTGCACACCTTCCCAG CTGTGCTGCAGAGCTCCGGCCTGTACAGCCTCTCTT CTGTGGTGACCGTGCCCTCTAGCAACTTCGGAACAC AGACCTACACATGTAACGTGGATCACAAGCCTTCC AACACCAAGGTGGATAAGACCGTGGAGAGAAAGTG CTGTGTGGAGTGCCCTCCATGTCCTGCCCCACCTGT GGCTGGACCTTCTGTGTTTCTGTTCCCTCCAAAGCC AAAGGATACCCTGATGATCAGCAGAACTCCTGAGG TGACCTGTGTGGTGGTGGACGTGAGCCACGAGGAT CCTGAGGTGCAGTTTAACTGGTACGTGGATGGCGTG GAGGTGCATAACGCTAAGACAAAGCCTAGGGAGGA GCAGTTTAACAGCACCTTCAGAGTGGTGAGCGTGCT GACCGTGGTGCACCAGGATTGGCTGAACGGCAAGG AGTATAAGTGTAAGGTGTCTAACAAGGGCCTGCCA GCCCCTATTGAGAAGACCATCAGTAAGACCAAGGG |

TABLE 2-continued

Amino acid sequences of heavy and light chains in three chimeric antibodies and nucleotide sequence coding therefor (bolds represent variable regions)

| | Amino acid sequence | Nucleotide sequence (cDNA) |
|---|---|---|
| | ID NO: 7) | ACAGCCTAGGGAGCCTCAGGTGTACACCCTGCCTCC<br>TTCCAGAGAGGAGATGACAAAGAACCAGGTGAGCC<br>TGACCTGTCTGGTGAAGGGCTTCTACCCTAGCGATA<br>TCGCCGTGGAGTGGGAGAGCAACGGCCAGCCTGAG<br>AACAACTACAAGACCACCCCACCTATGCTGGACAG<br>CGATGGCTCTTTCTTCCTGTACTCTAAGCTGACCGT<br>GGACAAGAGCAGATGGCAGCAGGGCAACGTGTTTT<br>CTTGTTCTGTGATGCACGAGGCCCTGCACAACCACT<br>ACACCCAGAAGTCTCTGTCTCTGTCTCCAGGCAAGT<br>GA (SEQ ID NO: 8) |
| Heavy<br>chain of<br>IgG4<br>chimeric<br>Ab<br>(comprising<br>human<br>IgG4<br>constant<br>region) | QVQMLQSGTELVRP<br>GTSVKVSCKASGYGF<br>TNYLIEWVKQRPGQ<br>GLEWIGVINPGYGGV<br>NYNEKFKGKAILTAD<br>KSSSTAYMHLTSLTS<br>DDSAVYFCARGGSGF<br>AFWGQGTLVTVSTA<br>STKGPSVFPLAPCSRST<br>SESTAALGCLVKDYFP<br>EPVTVSWNSGALTSG<br>VHTFPAVLQSSGLYSL<br>SSVVTVPSSSLGTKTY<br>TCNVDHKPSNTKVDK<br>RVESKYGPPCPPCPAP<br>EFLGGPSVFLFPPKPK<br>DTLMISRTPEVTCVVV<br>DVSQEDPEVQFNWYV<br>DGVEVHNAKTKPREE<br>QFNSTYRVVSVLTVLH<br>QDWLNGKEYKCKVS<br>NKGLPSSIEKTISKAKG<br>QPREPQVYTLPPSQEE<br>MTKNQVSLTCLVKGF<br>YPSDIAVEWESNGQPE<br>NNYKTTPPVLDSDGSF<br>FLYSRLTVDKSRWQE<br>GNVFSCSVMHEALHN<br>HYTQKSLSLSLGK<br>(SEQ ID NO: 9) | CAGGTACAGATGCTGCAGAGCGGAACTGAACTG<br>GTTAGACCTGGTACTAGCGTTAAGGTCAGCTGTA<br>AGGCTAGCGGATACGGTTTCACCAACTACCTGAT<br>CGAATGGGTCAAGCAGAGGCCAGGACAAGGTTT<br>GGAGTGGATTGGAGTGATTAACCCCGGGTATGG<br>GGGCGTGAATTACAATGAGAAGTTTAAAGGCAA<br>AGCCATACTGACCGCAGACAAATCAAGTAGTAC<br>CGCCTATATGCACCTGACCATCTTTGACATCTGAC<br>GATTCTGCCGTGTATTTTTGCGCCCGGGCGGG<br>AGTGGCTTTGCTTTTTGGGGCCAGGGCACACTT<br>GTGACTGTGTCTACAGCTTCCACCAAGGGCCCCTC<br>CGTGTTCCCTCTCGCCCCTTGCTCCAGATCCACCTCC<br>GAGTCTACCGCCGCTCTGGGCTGCCTGGTCAAGGAC<br>TACTTCCCCGAGCCTGTGACCGTGTCTTGGAACTCT<br>GGCGCACTGACCAGCGGCGTGCACACCTTCCCTGCC<br>GTGCTGCAGTCCTCCGGCCTGTACTCCCTGTCCTCC<br>GTCGTGACCGTGCCCTCCTCCAGCCTGGGCACCAAG<br>ACCTACACCTGTAACGTGGACCACAAGCCCTCCAA<br>CACCAAGGTGGACAAGCGGGTGGAATCTAAGTACG<br>GCCCTCCCTGCCCCCCCTGCCCTGCCCCTGAATTTCT<br>GGGCGGACCTTCCGTGTTCCTGTTCCCCCCAAAGCC<br>CAAGGACACCCTGATGATCTCCCGGACCCCCGAAG<br>TGACCTGCGTGGTGGTGGACGTGTCCCAGGAAGAT<br>CCCGAGGTCCAGTTCAATTGGTACGTGGACGGCGT<br>GGAAGTGCACAACGCCAAGACCAAGCCCAGAGAG<br>GAACAGTTCAACTCCACCTACCGGGTGGTGTCCGTG<br>CTGACCGTCCTGCACCAGGACTGGCTGAACGGCAA<br>AGAGTACAAGTGCAAGGTGTCCAACAAGGGCCTGC<br>CCTCCAGCATCGAAAAGACCATCTCCAAGGCCAAG<br>GGCCAGCCCCGCGAGCCTCAGGTGTACACCCTGCC<br>CCCTAGCCAGGAAGAGATGACCAAGAACCAGGTGT<br>CCCTGACCTGTCTCGTCAAAGGCTTCTACCCCTCCG<br>ATATCGCCGTGGAATGGGAGTCCAACGGCCAGCCC<br>GAGAACAACTACAAGACCACCCCCCCTGTGCTGGA<br>CTCCGACGGCTCCTTCTTTCTGTACTCTCGGCTGACC<br>GTGGATAAGAGCCGGTGGCAGGAAGGCAACGTCTT<br>CTCCTGCTCCGTGATGCACGAGGCCCTGCACAACCA<br>CTATACCCAGAAGTCCCTGTCCCTGAGCCTGGGCAA<br>ATGA (SEQ ID NO: 10) |
| Light<br>chain | DIQMTQTTSSLSASL<br>GQRVTISCRASQDISN<br>HLNWYQQKPNGTVR<br>LLISSTSRLHSGVPSR<br>FSGSGSGTDYSLTISN<br>LEQEDIATYFCQQGN<br>TLPWTFGGGTKLEIK<br>RTVAAPSVFIFPPSDEQ<br>LKSGTASVVCLLNNFY<br>PREAKVQWKVDNAL<br>QSGNSQESVTEQDSKD<br>STYSLSSTLTLSKADY<br>EKHKVYACEVTHQGL<br>SSPVTKSFNRGEC<br>(SEQ ID NO: 11) | GACATCCAAATGACCCAAACCACCTCCTCACTTT<br>CCGCATCTCTTGGACAAAGAGTCACCATCTCCTG<br>TAGGGCAAGTCAAGACATCTCCAACCACCTCAAC<br>TGGTACCAGCAGAAGCCAAACGGAACTGTTAGG<br>TTGTTGATCTCCAGCACCTCACGTTTGCACTCAG<br>GAGTACCATCACGATTCAGCGGTAGTGGTTCTG<br>GTACAGATTACAGCTTGACCATTAGCAACCTGGA<br>GCAGGAGGATATTGCTACCTACTTCTGCCAGCA<br>GGGCAATACCCTGCCTTGGACATTTGGGGGGGG<br>CACAAAACTGGAAATTAAGCGGACTGTTGCTGCTC<br>CATCTGTTTTTATATTTCCTCCCAGCGACGAGCAGC<br>TGAAAAGCGGCACTGCCTCTGTGGTGTCTGCTGA<br>ATAATTTTTACCCCCGGGAAGCCAAAGTCCAGTGG<br>AAGGTGGATAATGCCCTCCAGTCTGGGAACAGTCA<br>GGAAAGTGTGACAGAACAGGATAGTAAGGACTCTA<br>CTTATAGCCTCTCTTCTACACTGACTCTGTCAAAGG<br>CCGACTATGAGAAGCATAAAGTGTATGCCTGCGAG<br>GTGACACATCAGGGCCTGAGTTCACCCGTGACAAA<br>ATCTTTTAACCGCGGCGAGTGCTGA<br>(SEQ ID NO: 12) |

For use as a positive control antibody, the anti-CD40 human antibody CP870,893 (U.S. Pat. No. 7,338,660 B2; 21.4.1 antibody) was also synthesized. A pcDNA3.4 expression vector was constructed in the same manner. For use as a control, an antibody was constructed using the sequence information of CP870,893 antibody (U.S. Pat. No. 7,338,660 B2; 21.4.1 antibody) and named CP870,893 antibody analogue. The amino acid sequences and coding nucleotide sequences used to construct the CP870,893 antibody analogue are summarized in Table 3, below:

TABLE 3

Amino acid and nucleotide sequences of anti-CD40 human antibody CP870,893 (21.4.1 antibody) (signal sequences underlined and variable regions in bold)

| | Amino acid sequence | Nucleotide sequence (cDNA) |
|---|---|---|
| Heavy chain | MDWTWRILFLVAAATGA HSQVQLVQSGAEVKKP GASVKVSCKASGYTFTG YYMHWVRQAPGQGLE WMGWINPDSGGTNYAQ KFQGRVTMTRDTSISTA YMELNRLRSDDTAVYY CARDQPLGYCTNGVCS YFDYWGQGTLVTVSSAS TKGPSVFPLAPCSRSTSES TAALGCLVKDYFPEPVTV SWNSGALTSGVHTFPAVL QSSGLYSLSSVVTVPSSNF GTQTYTCNVDHKPSNTK VDKTVERKCCVECPPCPA PPVAGPSVFLFPPKPKDTL MISRTPEVTCVVVDVSHE DPEVQFNWYVDGVEVHN AKTKPREEQFNSTFRVVS VLTVVHQDWLNGKEYKC KVSNKGLPAPIEKTISKTK GQPREPQVYTLPPSREEM FK NQVSLTCLVKGFYPSDIA VEWESNGQPENNYKTTPP MLDSDGSFFLYSKLTVDK SRWQQGNVFSCSVMHEA LHNHYTQKSLSLSPGK (SEQ ID NO: 13) | ATGGACTGGACCTGGAGGATCCTCTTCTTGGTGGCAG CAGCCACAGGAGCCCACTCCCAGGTGCAGCTGGTGC AGTCTGGGGCTGAGGTGAAGAAGCCTGGGGCCTC AGTGAAGGTCTCCTGCAAGGCTTCTGGATACACCT TCACCGGCTACTATATGCACTGGGTGCGACAGGCC CCTGGACAAGGGCTTGAGTGGATGGGATGGATCA ACCCTGACAGTGGTGGCACAAACTATGCACAGAAG TTTCAGGGCAGGGTCACCATGACCAGGGACACGTC CATCAGCACAGCCTACATGGAGCTGAACAGGCTGA GATCTGACGACACGGCCGTGTATTACTGTGCGAGA GATCAGCCCCTAGGATATTGTACTAATGGTGTATG CTCCTACTTTGACTACTGGGGCCAGGGAACCCTGG TCACCGTCTCCTCAGCCTCCACCAAGGGCCCATCGG FCTTCCCCCTGGCGCCCTGCTCCAGGAGCACCTCCGA GAGCACAGCGGCCCTGGGCTGCCTGGTCAAGGACTAC FTCCCCGAACCGGTGACGGTGTCGTGGAACTCAGGCG CTCTGACCAGCGGCGTGCACACCTTCCCAGCTGTCCT ACAGTCCTCAGGACTCTACTCCCTCAGCAGCGTGGTG ACCGTGCCCTCCAGCAACTTCGGCACCCAGACCTACA CCTGCAACGTAGATCACAAGCCCAGCAACACCAAGGT GGACAAGACAGTTGAGCGCAAATGTTGTGTCGAGTGC CCACCGTGCCCAGCACCACCTGTGGCAGGACCGTCAG FCTTCCTCTTCCCCCCAAAACCCAAGGACACCCTCATG ATCTCCCGGACCCCTGAGGTCACGTGCGTGGTGGTGG ACGTGAGCCACGAAGACCCCGAGGTCCAGTTCAACTG GTACGTGGACGGCGTGGAGGTGCATAATGCCAAGAC AAAGCCACGGGAGGAGCAGTTCAACAGCACGTTCCGT GTGGTCAGCGTCCTCACCGTTGTGCACCAGGACTGGC FGAACGGCAAGGAGTACAAGTGCAAGGTCTCCAACA AAGGCCTCCCAGCCCCCATCGAGAAAACCATCTCCAA AACCAAAGGGCAGCCCCGAGAACCACAGGTGTACAC CCTGCCCCCATCCCGGGAGGAGATGACCAAGAACCAG GTCAGCCTGACCTGCCTGGTCAAAGGCTTCTACCCCA GCGACATCGCCGTGGAGTGGGAGAGCAATGGGCAGC CGGAGAACAACTACAAGACCACACCTCCCATGCTGGA CTCCGACGGCTCCTTCTTCCTCTACAGCAAGCTCACCG FGGACAAGAGCAGGTGGCAGCAGGGGAACGTCTTCTC ATGCTCCGTGATGCATGAGGCTCTGCACAACCACTAC ACGCAGAAGAGCCTCTCCCTGTCTCCGGGTAAATGA (SEQ ID NO: 14) |
| Light chain | MRLPAOLLGLLLLWFPGS RCDIQMTQSPSSVSASVG DRVTITCRASQGIYSWL AWYQQKPGKAPNLLIY TASTLQSGVPSRFSGSGS GTDFTLTISSLQPEDFAT YYCQQANIFPLTFGGGT KVEIKRTVAAPSVFIFPPS DEQLKSGTASVVCLLNNF YPREAKVQWKVDNALQS GNSQESVTEQDSKDSTYS LSSTLTLSKADYEKHKVY ACEVTHQGLSSPVTKSFN RGEC (SEQ ID NO: 15) | ATGAGGCTCCCTGCTCAGCTCCTGGGGCTCCTGCTGCT CTGGTTCCCAGGTTCCAGATGCGACATCCAGATGAC CCAGTCTCCATCTTCCGTGTCTGCATCTGTAGGAG ACAGAGTCACCATCACTTGTCGGGCGAGTCAGGGT ATTTACAGCTGGTTAGCCTGGTATCAGCAGAAACC AGGGAAAGCCCCTAACCTCCTGATCTATACTGCAT CCACTTTACAAAGTGGGGTCCCATCAAGGTTCAGC GGCAGTGGATCTGGGACAGATTTCACTCTCACCAT CAGCAGCCTGCAACCTGAAGATTTTGCAACTTACT ATTGTCAACAGGCTAACATTTTCCCGCTCACTTTCG GCGGAGGGACCAAGGTGGAGATCAAACGAACTGTG GCTGCACCATCTGTCTTCATCTTCCCGCCATCTGATGA GCAGTTGAAATCTGGAACTGCCTCTGTTGTGTGCCTGC FGAATAACTTCTATCCCAGAGAGGCCAAAGTACAGTG GAAGGTGGATAACGCCCTCCAATCGGGTAACTCCCAG GAGAGTGTCACAGAGCAGGACAGCAAGGACAGCACC TACAGCCTCAGCAGCACCCTGACGCTGAGCAAAGCAG ACTACGAGAAACACAAAGTCTACGCCTGCGAAGTCAC CCATCAGGGCCTGAGCTCGCCCGTCACAAAGAGCTTC AACAGGGGAGAGTGTTAG (SEQ ID NO: 16) |

1-2-2. Chimeric Anti-CD40 Antibody Production

For chimeric antibody production, expression vectors carrying three heavy chains (respectively comprising constant regions of human IgG1, human IgG2, and human IgG4) and one light chain (inclusive of the kappa constant regions) were introduced into the EXPICHO™ Expression system (Thrmofisher, Cat. No.: A29133) in a transient transformation manner to produce IgG1 chimeric antibody (inclusive of the constant region of human IgG1), IgG2 chimeric antibody (inclusive of the constant region of human IgG2), and IgG4 chimeric antibody (inclusive of the constant region of human IgG4).

The ExpiCHO-S cell line included within the EXPICHO™ Expression system kit (Termofisher, Cat. No.: A29133) was thawed and added to the Expression medium and incubated at 37° C. in a 8% $CO_2$ atmosphere with shaking at 120 rpm to secure a necessary number of cells. After being harvested, the ExpiCHO-S cells were seeded at a density of $6×10^6$ cells/mL in the Expression medium to a final volume of 150 mL. As indicated by the manual, 100 μg of the light chain vector and 50 μg of the heavy chain vector were mixed with OPTIPRO™ SFM and EXPI-FECTAMINE™ CHO reagent to give a mixture in which the vectors were at a concentration of 1.0 μg/mL with the light chain and the heavy chain maintained at a ratio of 2:1. The vector mixture prepared for transformation was added to the ExpiCHO-S cell line and incubated at 37° C. for 24 hours in 8% $CO_2$ atmosphere with shaking at 120 rpm. At 24 hours of incubation, the EXPICHO™ Enhancer and Feed were further added. On day five after incubation, the incubation condition was changed to 32° C., 5% $CO_2$, and 120 rpm. In the new condition, the cells were incubated with the EXPICHO™ Feed for an additional 12 days.

The culture medium thus obtained was sterilized by filtration and loaded into HITRAP® Protein A HP column (GE Healthcare, Cat. No.: 11-0034-93) equilibrated with Protein A equilibration buffer (20 mM phosphate, pH7.4) and washed by flowing the equilibration buffer through the column, followed by antibody recovery with an elution buffer (20 mM Citric acid pH3.0). The recovered antibody was dialyzed against phosphate buffered saline to exchange the buffer for use in subsequent tests.

1-2-3. Assay for Antigen Binding Force of Chimeric Anti-CD40 Antibody

The three anti-CD40 chimeric antibodies IgG1, IgG2, and IgG4 constructed in Examples 1-2-2 were assayed for antigen reactivity by ELISA. A dilution of the recombinant antigen human CD40 (Sino Biological Inc., Cat. No.: 10774-H02H) at a concentration of 1.0 μg/mL in phosphate buffered saline was plated at 100 μL/well into microplates and incubated at 37° C. for one hour to coat the plates therewith. Then, a 1× blocking solution (Sigma) was added in an amount of 200 μL per well and incubated at 37° C. for one hour to block the antigen.

Each of the three anti-CD40 chimeric antibodies and the control antibody anti-CD40 human antibody CP870,893 analogue (21.4.1 antibody in Table 2) was serially diluted from a concentration of 10.0 μg/mL. The dilutions were added in an amount of 100 μL/well, incubated at 37° C. for one hour and washed three times with phosphate buffered saline. The antibodies were treated with the secondary antibody goat anti-human IgG F(ab')2-HRP (Jackson Immunoresearch, Cat. No.: 109-035-006) at 37° C. for 30 min and washed three times with phosphate buffered saline. After reaction with 100 μL of TMB Single Solution (Life Technologies, Cat. No: 002023) per well at room temperature for 4-10 min in a dark place, the color development was stopped with 100 μL of 1.0 N sulfuric acid and then absorbance at 450 nm was measured.

Figure 2:
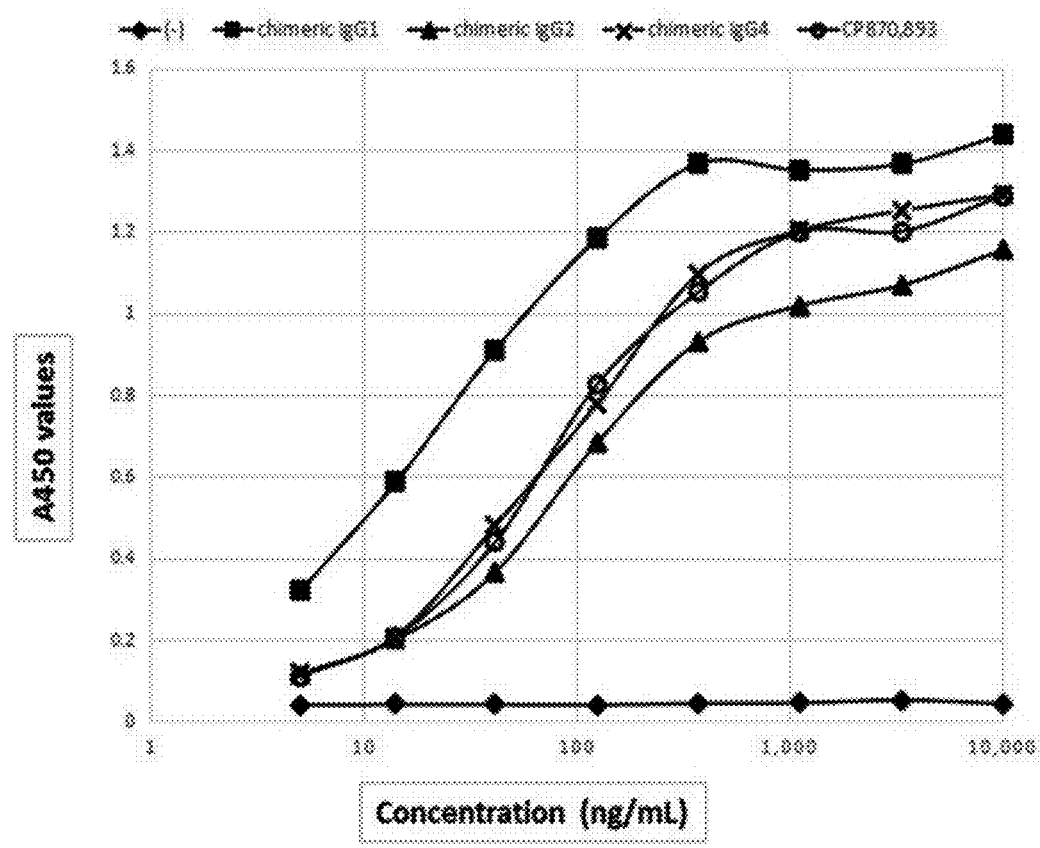
FIG. 2 is a graph showing binding affinity of 3 anti-CD40 5C2 chimeric antibodies to CD40 (Chimeric IgG1: a chimeric antibody comprising human IgG1 constant region; Chimeric IgG2: a chimeric antibody comprising human IgG2 constant region; Chimeric IgG4: a chimeric antibody comprising human IgG4 constant region; CP870,893: control antibody; (−): without antibody treatment).

Absorbance at 450 nm of the chimeric antibodies thus obtained are depicted in FIG. 2. ((–) denotes a control treated with no antibodies). As shown in FIG. 2, all the three anti-CD40 chimeric antibodies were found to have affinity for CD40 as high as or higher than that the control antibody.

1-3. Preparation of Humanized Antibody

On the basis of the amino acid sequence of the anti-CD40 mouse antibody 5C2, an anti-CD40 humanized antibody was constructed.

1-3-1. Selection of Recombinant Antibody Sequence by in Silico Humanization

Humanized antibody sequences that retained CDR region sequences of each of the heavy and light chains of mouse CD40 antibody 5C2 and in which on the basis of a germline sequence of a human antibody gene, sequences for the framework region were recombined were selected in an in-silico manner.

To begin with, heavy-chain CDRs (complementarity determining regions) and light-chain CDRs were determined on the basis of the heavy- and light-chain variable regions of the anti-CD40 mouse antibody 5C2 introduced in Table 1 (referring to IMGT/V-QUEST and are summarized in Table 4, below:

TABLE 4

| | CDR1 | CDR2 | CDR3 |
|---|---|---|---|
| Determined according to IMGT/V-QUEST (http://www.imgt.org/IMGT_vquest/share/textes/) | | | |
| Heavy chain | GYGFTNYL (SEQ ID NO: 17) | INPGYGGV (SEQ ID NO: 18) | GGSGFAF (SEQ ID NO: 19) |
| Light chain | QDISNH (SEQ ID NO: 20) | STS (SEQ ID NO: 21) | QQGNTLP (SEQ ID NO: 22) |
| Determined according to Cabat definition (http://www.bioinf.org.uk/abs/) | | | |
| Heavy chain | NYLIE (SEQ ID NO: 33) | VINPGYGGVNYNEKFKG (SEQ ID NO: 34) | GGSGFAF (SEQ ID NO: 19) |
| Light chain | RASQDISNHLN (SEQ ID NO: 35) | STSRLHS (SEQ ID NO: 36) | QQGNTLP (SEQ ID NO: 22) |

In Table 5 are summarized human antibody germline genes that were employed as the backbones of humanized recombinant antibody sequences because of the highest similarity in sequence to each of the heavy and light chains of mouse CD40 antibody 5C2:

TABLE 5

Human Antibody Germline Gene Used for
Humanization of Mouse 5C2 Antibody
Human Ab Germline

| Heavy chain | Light chain |
|---|---|
| IGHV1-2*02 | IGKV1-NL1*01 |
| IGHV1-69*06 | IGKV3-15*01 |
| IGHV5-51*01 | — |

Six heavy-chain variable regions and two light-chain variable regions for humanized 5C2 antibodies were selected in an in-silico method using the human antibody germline gene sequences and are summarized in Table 6, below:

TABLE 6

5C2 humanized antibody variable region sequence selected in silico

| | Class | Sequence | SEQ ID NO: |
|---|---|---|---|
| Heavy chain variable region | VH1 | QVQLVQSGAEVKKPGASVKVSCKASGYGFTNYLIEWVRQAP GQGLEWIGVINPGYGGVNYNEKFKGRATLTADKSISTAYMEL SRLRSDDTAVYFCARGGSGFAFWGQGTLVTVSS | 23 |
| | VH2 | QVQLVQSGAEVKKPGASVKVSCKASGYGFTNYLIEWVRQAP GQGLEWIGVINPGYGGVNYNEKFKGRVTLTADKSISTAYMEL SRLRSDDTAVYFCARGGSGFAFWGQGTLVTVSS | 24 |
| | VH3 | QVQLVQSGAEVKKPGSSVKVSCKASGYGFTNYLIEWVRQAPG QGLEWIGVINPGYGGVNYNEKFKGRATLTADKSTSTAYMELS SLRSEDTAVYFCARGGSGFAFWGQGTLVTVSS | 25 |
| | VH4 | QVQLVQSGAEVKKPGSSVKVSCKASGYGFTNYLIEWVRQAPG QGLEWIGVINPGYGGVNYNEKFKGRVTITADKSTSTAYMELSS LRSEDTAVYFCARGGSGFAFWGQGTLVTVSS | 26 |
| | VH5 | EVQLVQSGAEVKKPGESVKISCKASGYGFTNYLIEWVROMPG KGLEWIGVINPGYGGVNYNEKFKGQATLSADKSISTAYLQLSS LKASDTAVYFCARGGSGFAFWGQGTLVTVSS | 27 |
| | VH6 | EVQLVQSGAEVKKPGESLKISCKASGYGFTNYLIEWVRQMPG KGLEWIGVINPGYGGVNYNEKFKGQVTISADKSISTAYLQLSS LKASDTAMYFCARGGSGFAFWGQGTLVTVSS | 28 |
| Light variable region Chain | VL1 | DIQMTQSPSSLSASVGDRVTITCRASQDISNHLNWYQQKPGKA VKLLISSTSRLHSGVPSRFSGSGSGTDYTLTISSLQPEDFATYFC QQGNTLPWTFGQGTKVEIK | 29 |
| | VL2 | EIVMTQSPATLSVSPGERATLSCRASQDISNHLNWYQQKPGOA VRLLISSTSRLHSGIPARFSGSGSGTEYTLTISSLQSED-FAVYFCQ QGNTLPWTFGQGTKVEIK | 30 |

(CDR1, CDR2, are CDR3 (according to the IMGT definition) are sequentially underlined)

1-3-2. Expression and Analysis of Humanized Recombinant Antibody

The heavy-chain variable region sequences in-silico selected were linked to the human IgG2 constant region to complete heavy-chain sequences while the light-chain variable region sequences were linked to the kappa light-chain constant region to complete light-chain sequences. The selected amino acid sequences were converted into genetic sequences coding therefor and gene fragments having the sequences are synthesized (Cosmogenetech).

The coding gene fragments of heavy and light chains prepared above were transferred into respective pCDNA3.4 vectors. Four heavy chains (VH1, VH2, VH3, VH5) and two light chains (L1, L2) were combined to make eight humanized antibodies (VH1VL1: a combination of VH1 and VL1; VH2VL1: a combination of VH2 and VL1; VH3VL1: a combination of VH3 and VL1; VH5VL1: a combination of VH5 and VL1; VH6VL1: a combination of VH6 and VL1; VH1VL2: a combination of VH1 and VL2; VH2VL2: a combination of VH2 and VL2; VH3VL2: a combination of VH3 and VL2; VH5VL2: a combination of VH5 and VL2; VH6AVL2: a combination of VH6 and VL2). The antibodies were introduced to be expressed in CHO cells (Sigma, Cat. #: 85050302) with the aid of VIAFECT™ Transfection Reagent (Promega, Cat. No.: D4981) and incubated for an additional two day before taking the supernatants.

Each of the humanized antibody cultures was assayed for reactivity for a recombinant antigen human CD40 (rCD40; R&D systems, Cat. No.: P25942) by ELISA. For this assay, a dilution of rCD40 at a concentration of 1.0 μg/mL in phosphate buffered saline was plated at a density of 100 μL/well into microplates and incubated at 37° C. for one hour to coat the microplates with the antigen which was then blocked by adding a 1× blocking solution (Sigma) in an amount of 200 μl per well and incubating at 37° C. for one hour.

Following one hour of incubation with 100 μL of each of the humanized anti-CD40 antibody cultures at 37° C., the microplates were washed three times with phosphate buffered saline. Treatment with the secondary antibody goat anti-human IgG F(ab')2-HRP (Jackson Immunoresearch, Cat. No.: 109-035-006) at 37° C. for 30 min was followed by three rounds of washing with phosphate buffered saline. Then, TMB Single Solution (Life Technologies, Cat. No: 002023) was added in an amount of 100 μl per well and incubated at room temperature for 5-10 min in a dark place. Color development was stopped with 100 μL of 1.0 N sulfuric acid and absorbance at 450 nm was measured.

Figure 3:
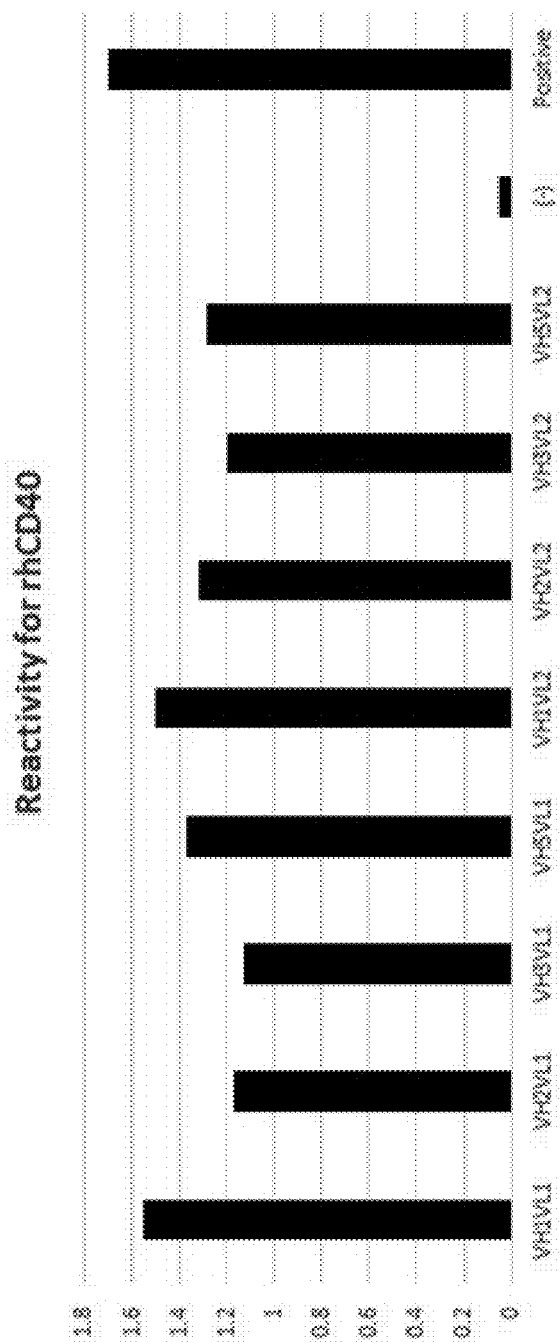
FIG. 3 is a graph showing binding affinity of 8 humanized 5C2 antibodies to human CD40 (VH1VL1: a combination of heavy chain VH1 and light chain VL1; VH2VL1: a combination of heavy chain VH2 and light chain VL1; VH3VL1: a combination of heavy chain VH3 and light chain VL1; VH5VL1: a combination of heavy chain VH5 and light chain VL1; VH1VL2: a combination of heavy chain VH1 and light chain VL2; VH2VL2: a combination of heavy chain VH2 and light chain VL2; VH3VL2: a combination of heavy chain VH3 and light chain VL2; VH5VL2: a combination of heavy chain VH5 and light chain VL2; (−): antibody-untreated group; Positive: chimeric 5C2 antibody comprising human IgG4 constant region).

Absorbances at 450 nm of the eight humanized antibodies are depicted in FIG. 3. As shown in FIG. 3, all the eight humanized antibodies were observed to have high reactivity for CD40.

Example 2: Effect of Anti-CD40 Antibody 5C2 on CD40/CD40L Binding Affinity

A blocking test was performed so as to examine whether the 5C2 antibody (mouse antibody) has an influence on interaction between CD40 and CD40L in the human body.

For buffer change, the 5C2 antibody and the isotype control antibody (Dinona, Cat. No.: 88020R) were each dialyzed against 0.1M sodium bicarbonate buffer and 1.0 mg of each antibody solution was prepared. A solution of FITC Isomer I (Invitrogen, Cat. No.: F1906) at a concentration of 2.6 mg/mL in DMSO (Sigma-Aldrich, Cat. No.: 276855) was added in an amount of 20.0 µL to each of the antibody solutions. After FITC conjugation by stirring at room temperature for 2 hours, the resulting antibody solutions were dialyzed against phosphate buffered saline to obtain FITC-labeled antibodies.

Then, $5 \times 10^6$ cells of Ramos cell line (ATCC, ATCC CRL-1596), which expresses human CD40, was incubated at room temperature for 30 min with 100 µL of a dilution of the recombinant antigen CD40L (Peprotech, Cat. No.: 310-02) at a concentration of 15.0 µg/mL. After washing with phosphate buffered saline, the cells were reacted with 1.0 µg/mL of each of the prepared FITC-labeled 5C2 and FITC-labeled isotype antibodies at room temperature for 15 min. The cells were washed again with phosphate buffered saline and then subjected to fluorescent immunoassay using flow cytometry (Strategdim, S1000EXi).

Figure 4:
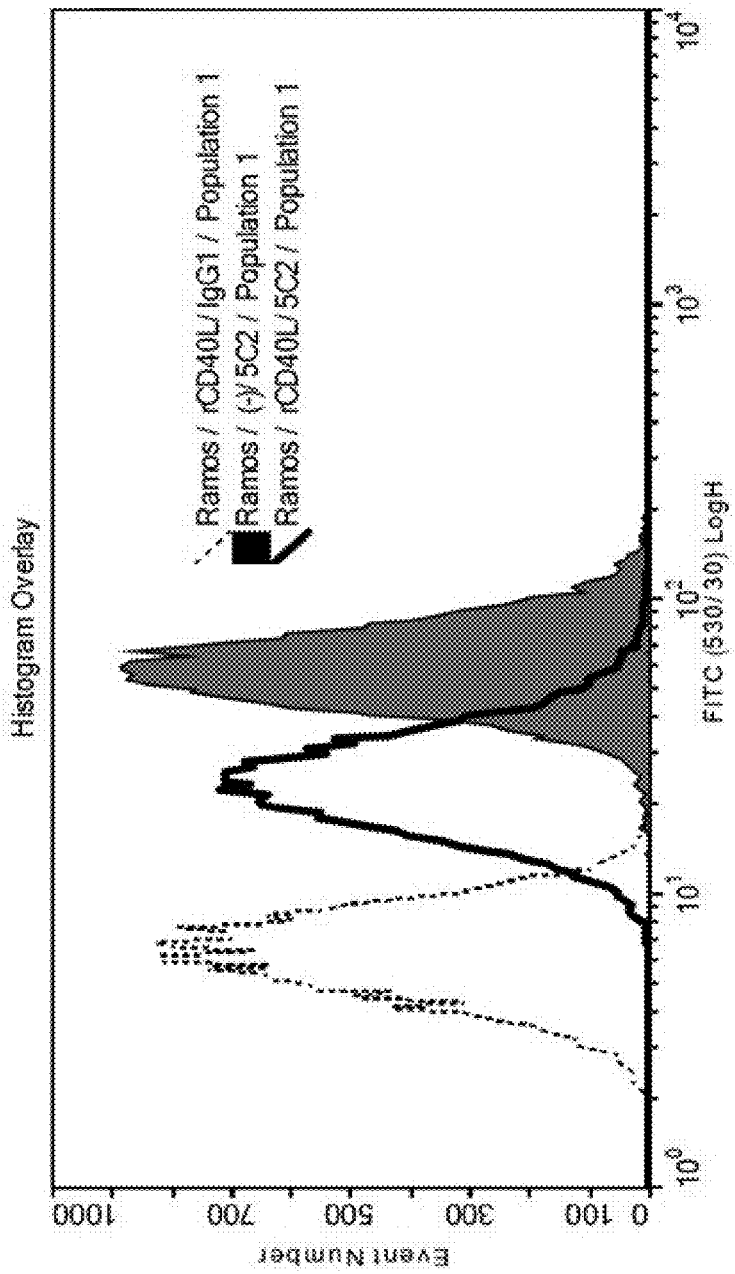
FIG. 4 shows the results of flow cytometry to examine the effects of anti-CD40 monoclonal antibody 5C2 on CD40/CD40L interaction.

The flow cytometry analysis results thus obtained are depicted in FIG. 4. As shown in FIG. 4, the fluorescence of FITC-labeled 5C2 was still generated although it was a little bit lower upon preincubation with the recombinant antigen CD40L than without CD40L because of the steric hinderance of the FITC-labeled 5C2. The results imply that the 5C2 antibody recognizes CD40 at a site different from the site of CD40/CD40L interaction.

Example 3: Assay for Activation of Dendrocyte

3-1. Preparation of Monocyte-Derived Dendrocyte

In order to examine whether the anti-CD40 antibody activates dendrocytes, monocyte-derived dendrocytes were prepared by differentiation and used for testing the efficacy of the anti-CD40 antibody.

Whole blood sampled from a healthy adult volunteer was transferred to an EDTA (ethylenediaminetetraacetic acid)-treated tube and mixed with one volume of phosphate buffered saline. The whole blood mixture was loaded on FICOLL® PAQUE PLUS (GE Healthcare, Cat. No.: 17-1440-03) and centrifuged at 700×g at room temperature for 30 min. After centrifugation, only the PBMC (peripheral blood mononuclear cell) layer was transferred to a new tube and added with about two volumes of phosphate buffered saline. Centrifugation at 4° C. at 700 g for 5 min formed a PBMC pellet. A suspension of the PBMC pellet in a 10% fetal bovine serum-supplemented RPMI medium was cultured at 37° C. for 4 hours in a cell culture dish (VOM plastic crop., Cat. No.: V100D) with 5% $CO_2$.

After removal of non-adherent cells from the cell culture dish, a fresh 10% fetal bovine serum-supplemented RPMI was added to the dish. For differentiation to dendrocytes, the adherent cells were incubated with $5 \times 10^3$ unit/mL of each of rhGM-CSF (Recombinant Human Granulocyte Macrophage Colony Stimulating Factor; JW creagene) and rhIL-4 (JW creagene). On days 3 and 6 after incubation, the 10% fetal bovine serum-supplemented RPMI medium was changed with a fresh one, with each of rhGM-CSF and rhIL-4 added at a concentration of $5 \times 10^3$ unit/mL.

On day 7 of differentiation, the dendrocytes were detached with trypsin-EDTA buffer (Thermo, Cat. No.: R001100), washed with a 10% fetal bovine serum-supplemented RPMI medium, and aliquoted into 24- or 12-well cell culture dishes. The cells were treated with the anti-CD40 antibody and various reagents according to test purposes and cultured for an additional 2 to 5 days before analysis of changes in the dendrocytes

3-2. Activation of Dendrocyte by Mouse Monoclonal 5C2

$5 \times 10^5$ cells of the monocyte-derived dendrocytes prepared in Example 3-1 were treated with 10 µg/mL of the mouse monoclonal antibody 5C2, together with the secondary antibody goat anti-mouse IgG (H+L) (Dionona) for crosslinking so as to amplify the efficacy.

After incubation with the antibody at 37° C. for 2 days in a 5% $CO_2$ atmosphere, the dendrocytes were detached with trypsin-EDTA (Thermo, Cat. No.: R001100). Dendrocytes were identified by immunostaining with an anti-CD11c antibody-FITC (eBiosceince, Cat. No.: 11-0116-42). Degrees of activation of the dendrocytes were accounted for by expression levels of the co-stimulatory factors CD80, CD83, and CD86 which were measured as fluorescence intensities detected after staining the cells with each of anti-CD80 antibody-PECy5 (eBiosceince, Cat. No.: 15-0809-42), anti-CD86 antibody-PE (eBiosceince, Cat. No.: 12-0869-42), and anti-CD83 antibody-APC (eBiosceince, Cat. No.: 17-0839-42).

Figure 5:
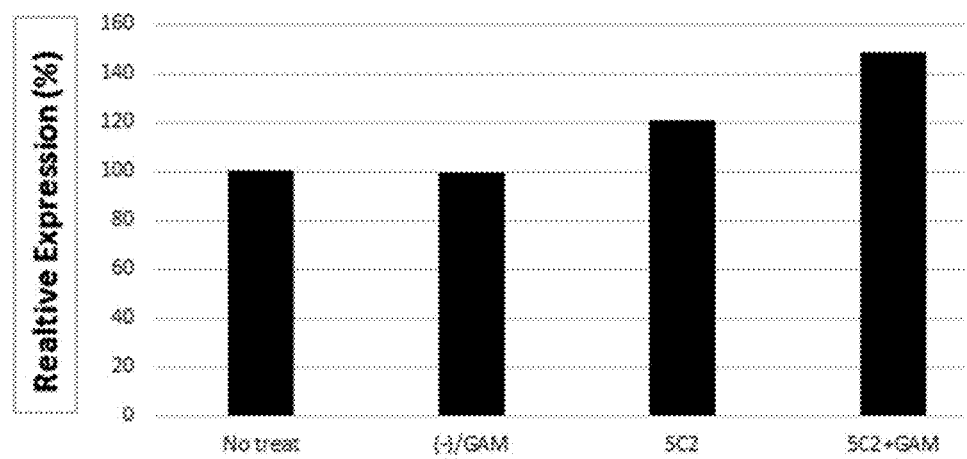
FIG. 5 is a graph showing the expression level of CD80 in dendrocytes treated with monoclonal antibody 5C2, wherein the expression level is indicated as a relative value to that of a control group (no treat: antibody-untreated group).
Figure 6:
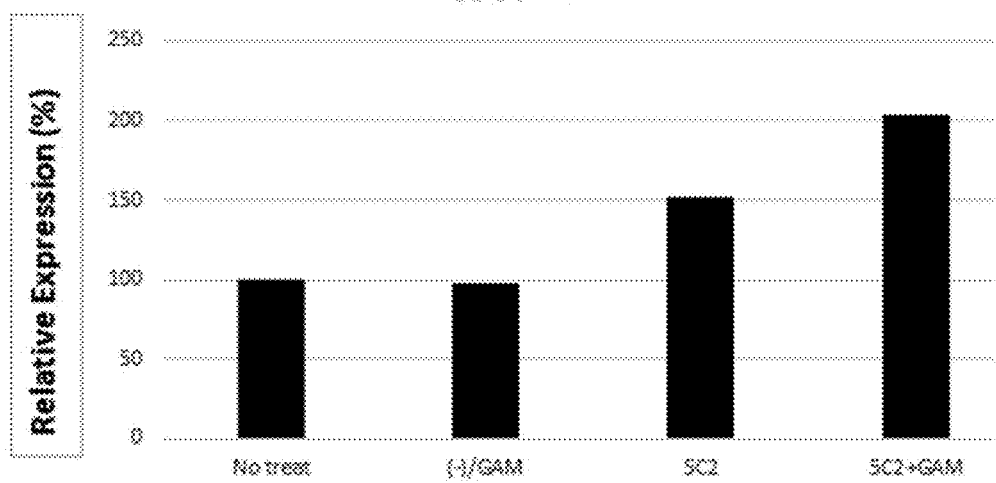
FIG. 6 is a graph showing the expression level of CD86 in dendrocytes treated with monoclonal antibody 5C2, wherein the expression level is indicated as a relative value to that of a control group (no treat: antibody-untreated group).
Figure 7:
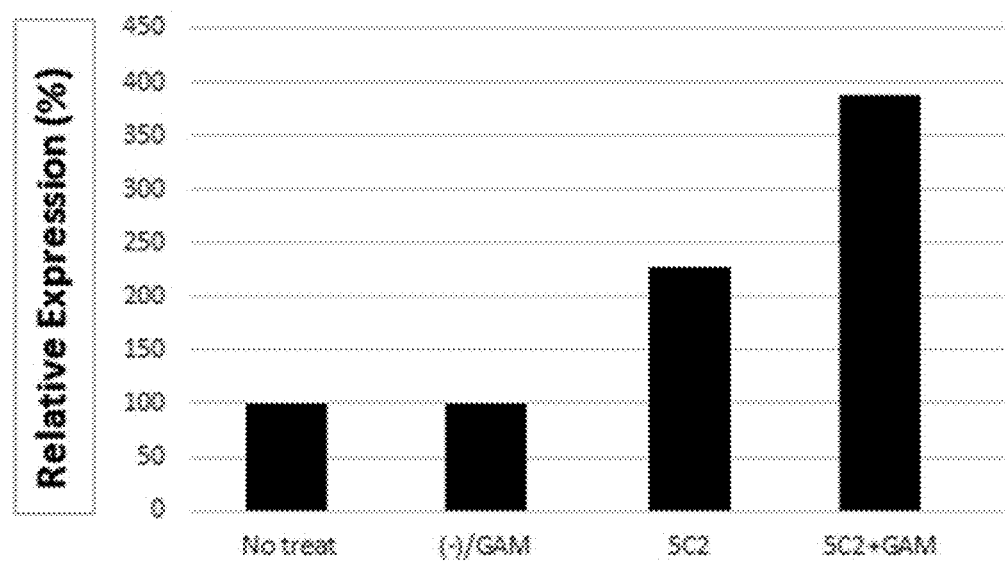
FIG. 7 is a graph showing the expression level of CD83 in dendrocytes treated with monoclonal antibody 5C2, wherein the expression level is indicated as a relative value to that of a control group (no treat: antibody-untreated group).

The fluorescence intensities obtained above are depicted as relative values to a control (not treated with the antibody, 100%) in FIG. 5 (relative expression level of CD80), FIG. 6 (relative expression level of CD86) and FIG. 7 (relative expression level of CD83) (in FIGS. 5 to 7, GAM denotes the secondary antibody goat anti-mouse IgG (H+L)). As shown in FIGS. 5 to 7, the 5C2 monoclonal antibody was found to induce the overexpression of the co-stimulatory factors CD80, CD83, and CD86, with the effect further enhanced by crosslinking with the secondary antibody.

3-3. Effect of Toll-like Receptor Ligand Used in Combination on Activation of Dendrocyte Toll-like receptors (TLRs) are usually expressed on sentinel cells, such as macrophages and dendrocytes, which account for innate immunity. The proteins are responsible for the function of recognizing molecules derived from microbes and activating innate immunity. Lipopolysaccharide (LPS), known as a TLR ligand recognized by TLR-4, was used in combination with the 5C2 antibody in order to evaluate the activation of dendrocytes.

For this, $5 \times 10^5$ cells of the monocyte-derived dendrocytes prepared in Example 3-1 were incubated for two days with 1.0 ng/mL of LPS (Sigma-Aldrich, Cat. No.: L3024) in combination of 10 µg/mL of 5C2 and 20 µg/mL of a secondary antibody goat anti-Mouse IgG(H+L) (Dionona), followed by detaching the dendrocytes with trypsin-EDTA. The dendrocytes were stained with anti-CD11c-FITC (eBiosceince, Cat. No.: 11-0116-42).

Degrees of activation of the dendrocytes were accounted for by expression levels of the co-stimulatory factors CD80 and CD83 which were measured as fluorescence intensities detected after staining the cells with each of anti-CD80 antibody-PECy5 (eBiosceince, Cat. No.: 15-0809-42) and anti-CD86 antibody-PE (eBiosceince, Cat. No.: 12-0869-42).

Figure 8:
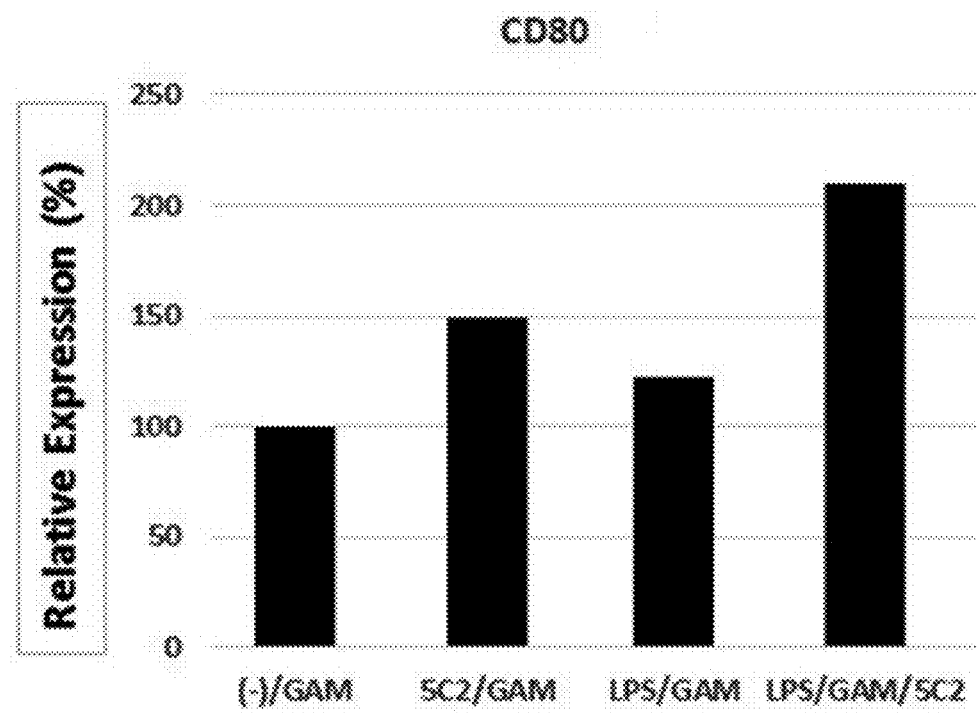
FIG. 8 is a graph showing the expression level of CD80 when cells are co-treated with Toll like receptor ligand (Lipopolysaccharid; LPS) and monoclonal antibody 5C2, wherein the expression level is indicated as a relative value to that of a control group (antibody-untreated group).
Figure 9:
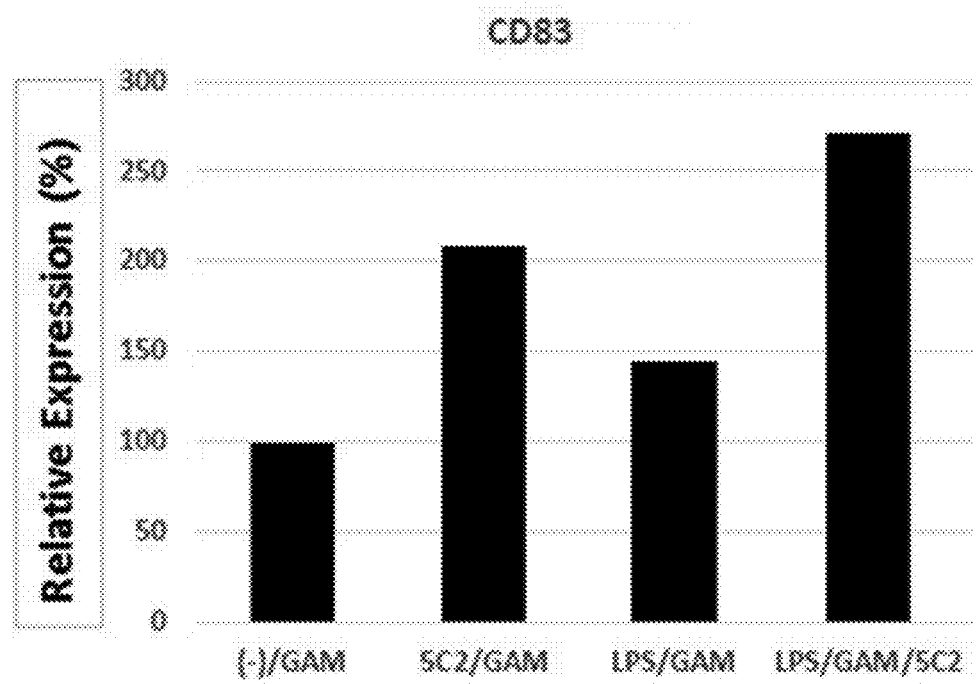
FIG. 9 is a graph showing the expression level of CD83 when cells are co-treated with Toll like receptor ligand (Lipopolysaccharid; LPS) and monoclonal antibody 5C2, wherein the expression level is indicated as a relative value to that of a control group (antibody-untreated group).

The fluorescence intensities obtained above are depicted as relative values to a control (not treated with the antibody, 100%) in FIG. 8 (relative expression level of CD80) and FIG. 9 (relative expression level of CD86) (in FIGS. 8 and 9, GAM denotes the secondary antibody goat anti-mouse IgG (H+L)). As shown in FIGS. 8 and 9, LPS alone induced overexpression of CD80 and CD83, but the overexpression of CD80 and CD83 was remarkably enhanced by LPS in the condition of crosslinking 5C2.

3-4. Activation of Dendrocyte by Chimeric 5C2

Dendrocytes which were differentiated from $5\times10^5$ monocytes as described in Example 3-1 were treated with 10 μg/mL of each of the two chimeric 5C2 antibodies (chimeric IgG2 and chimeric IgG4) and the CP870,893 analogue (U.S. Pat. No. 7,338,660 B2; 21.4.1 antibody; refer to Table 3) in the absence of a second antibody. After incubation at 37° C. for 5 days in a 5% $CO_2$ atmosphere, the dendrocytes were detached with trypsin-EDTA(Thermo, Cat. No.: R001100).

Dendrocytes were identified by immunostaining with an anti-CD11c antibody-FITC (eBiosceince, Cat. No.: 11-0116-42). Degrees of activation of the dendrocytes were accounted for by expression levels of the co-stimulatory factors CD80, CD83, and CD86 which were measured as fluorescence intensities detected after staining the cells with each of anti-CD80 antibody-PECy5 (eBiosceince, Cat. No.: 15-0809-42), anti-CD86 antibody-PE (eBiosceince, Cat. No.: 12-0869-42), and anti-CD83 antibody-APC (eBiosceince, Cat. No.: 17-0839-42).

Figure 10:
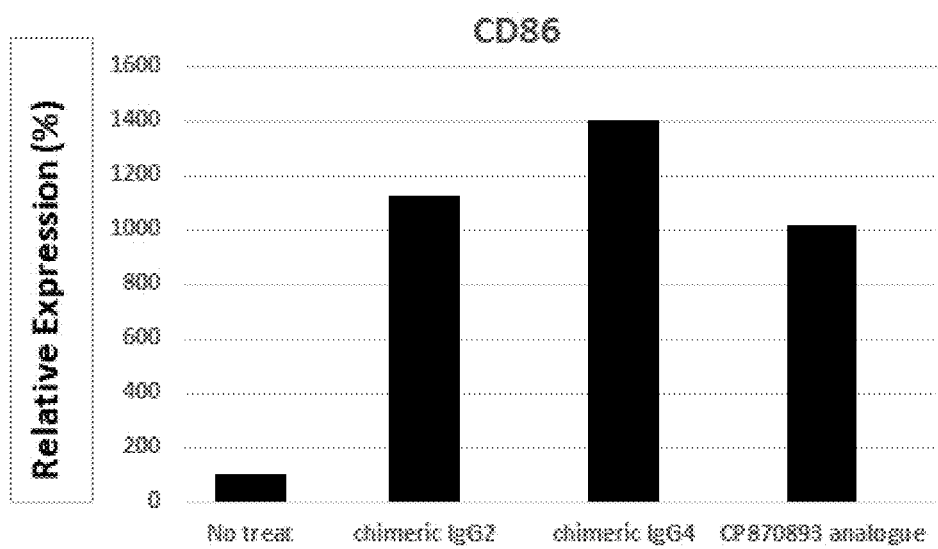
FIG. 10 is a graph showing the expression level of CD86 when cells are treated with human IgG1 chimeric antibody (chimeric IgG1), human IgG2 chimeric antibody (chimeric IgG2), and human IgG4 chimeric antibody (chimeric IgG4) of monoclonal antibody 5C2, wherein the expression level is indicated as a relative value to that of a control group (no treat: antibody-untreated group).
Figure 11:
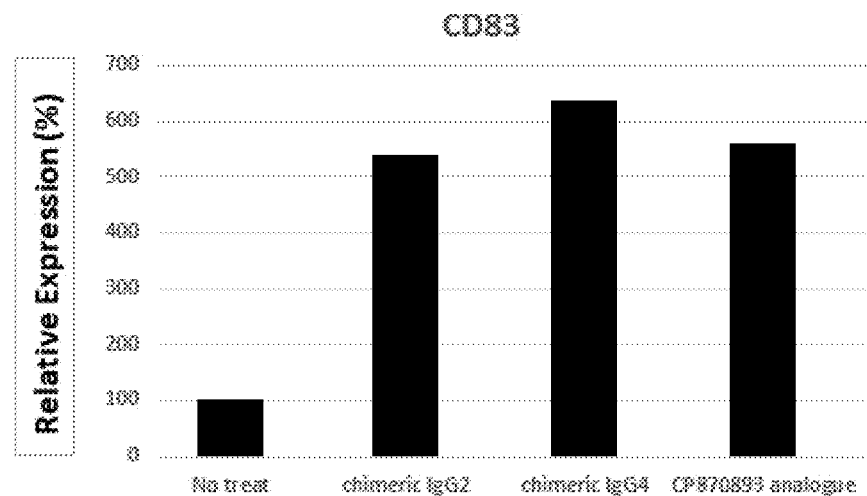
FIG. 11 is a graph showing the expression level of CD83 when cells are treated with human IgG1 chimeric antibody (chimeric IgG1), human IgG2 chimeric antibody (chimeric IgG2), and human IgG4 chimeric antibody (chimeric IgG4) of monoclonal antibody 5C2, wherein the expression level is indicated as a relative value to that of a control group (no treat: antibody-untreated group).

The fluorescence intensities obtained above are depicted as relative values to a control (not treated with the antibody, 100%) in FIG. 10 (relative expression level of CD86) and FIG. 11 (relative expression level of CD83).

The three 5C2-derived chimeric antibodies were observed to be not much different in reactivity for human CD40 because of the identical variable region thereof (FIG. 2), but to differ in the activation of dendrocytes from one isotype to another. For the mouse 5C2 antibody, a crosslinking antibody was indispensable for inducing the overexpression of the co-stimulatory factors, but the chimeric antibodies in IgG2 or IgG4 type were found to elicit the overexpression of CD86 and CD83 on dendrocytes even in the absence of a crosslinking antibody. Further, the 5C2 IgG4 chimeric antibody exhibited higher activation of dendrocyte, compared to the Pfizer analogue CP870,893, which is known as the best inducer for the activation of dendrocytes.

3-5. Synergistic Effect of IFN-Gamma on Activation of Dendrocytes

Dendrocytes indispensably requires interferon gamma for inducing T cell activation to effectively attack foreign matter or cancer cells, and interferon gamma is known to be directly involved in dendritic differentiation.

In order to examine the effect of the 5C2 chimeric antibody on dendrocyte activation and cytokine change in the presence of interferon gamma (IFN), interferon gamma (Pepprotech, Cat. No.: 300-02) was added at a concentration of 1000 unit/mL to the $5\times10^5$ monocyte-derived dendrocyte prepared in Example 3-1.

To the resulting cells, each of the two chimeric 5C2 antibodies (chimeric IgG2 and chimeric IgG4) and the CP870,893 analogue (U.S. Pat. No. 7,338,660 B2; 21.4.1 antibody; refer to Table 3) was added at a concentration of 10.0 μg/mL.

The dendrocytes were incubated with the antibodies at 37° C. for 2 days in a 5% $CO_2$ atmosphere and then detached with trypsin-EDTA (Thermo, Cat. No.: R001100). Dendrocytes were identified by immunostaining with an anti-CD11c antibody-FITC (eBiosceince, Cat. No.: 11-0116-42). Degrees of activation of the dendrocytes were accounted for by expression levels of the co-stimulatory factors CD86 and CD83 which were measured as fluorescence intensities detected after staining the cells with each of anti-CD86 antibody-PE (eBiosceince, Cat. No.: 12-0869-42) and anti-CD83 antibody-APC (eBiosceince, Cat. No.: 17-0839-42).

Figure 12:
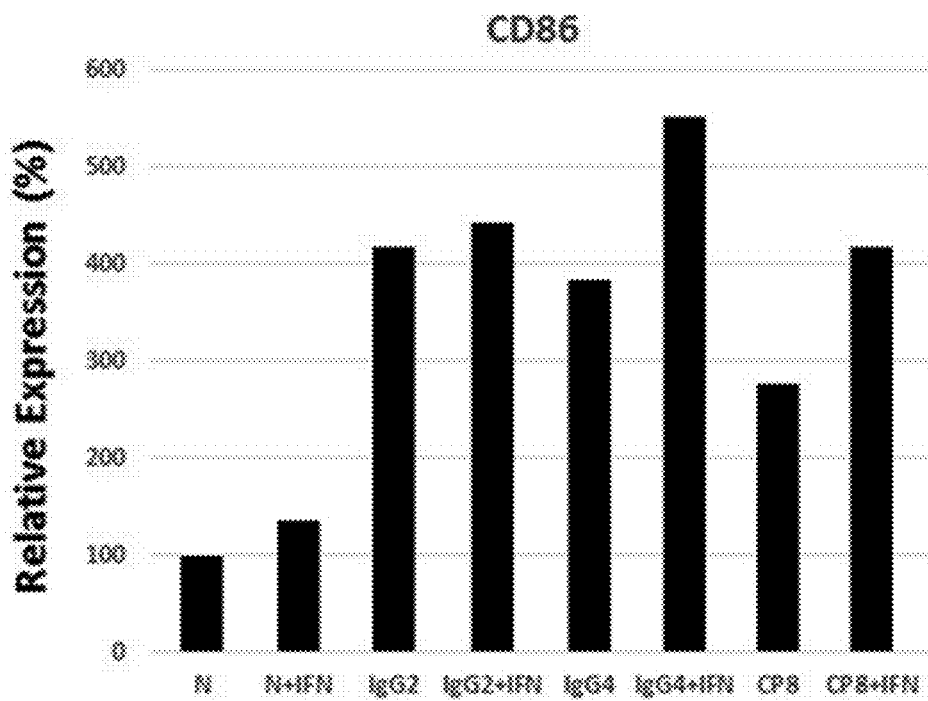
FIG. 12 is a graph showing the expression level of CD86 when cells are co-treated with interferon gamma together with human IgG1 chimeric antibody (chimeric IgG1), human IgG2 chimeric antibody (chimeric IgG2), and human IgG4 chimeric antibody (chimeric IgG4) of monoclonal antibody 5C2, wherein the expression level is indicated as a relative value to that of a control group (no treat: antibody-untreated group).
Figure 13:
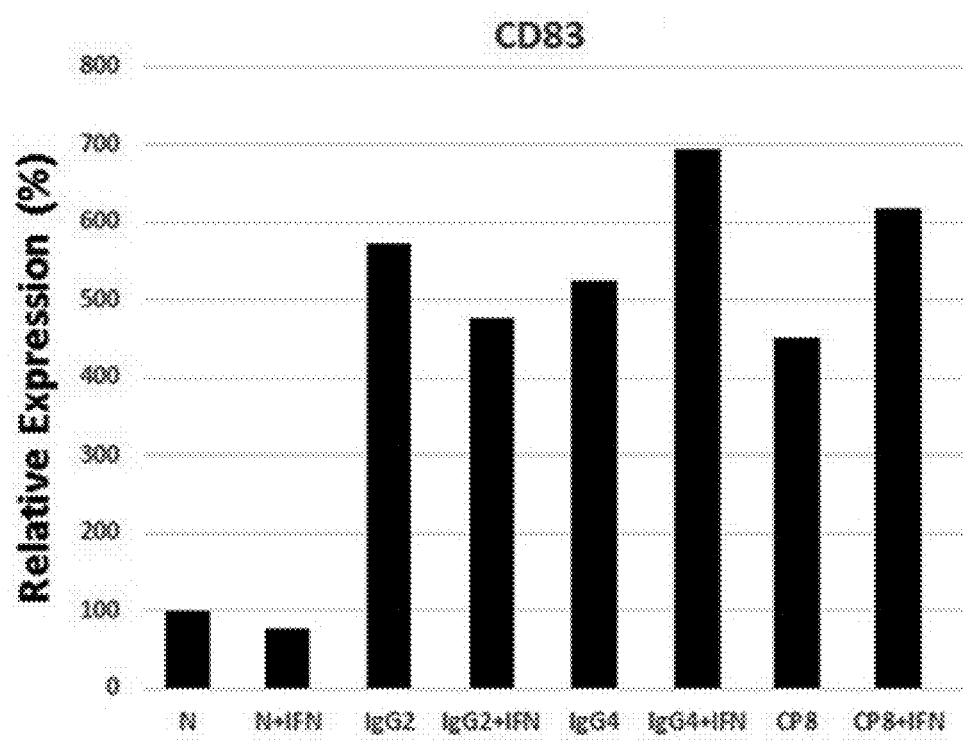
FIG. 13 is a graph showing the expression level of CD83 when cells are co-treated with interferon gamma together with human IgG1 chimeric antibody (chimeric IgG1), human IgG2 chimeric antibody (chimeric IgG2), and human IgG4 chimeric antibody (chimeric IgG4) of monoclonal antibody 5C2, wherein the expression level is indicated as a relative value to that of a control group (no treat: antibody-untreated group).

The fluorescence intensities obtained above are depicted as relative values to a control (not treated with the antibody, 100%) in FIG. 12 (relative expression level of CD86) and FIG. 13 (relative expression level of CD83) (N: treated with neither antibody nor interferon gamma, N+IFN: treated with interferon gamma alone, IgG2: treated with IgG2 chimeric antibody alone, IgG2+IFN: treated with IgG2 chimeric antibody and interferon gamma in combination, IgG4: treated with IgG4 chimeric antibody alone, IgG4+IFN: treated with IgG4 chimeric antibody and interferon gamma in combination, CP8: treated with CP870,893 analogue alone, and CP8+IFN: treated with CP870,893 analogue and interferon gamma in combination).

As shown in FIGS. 12 and 13, interferon gamma was observed to induce the overexpression of CD86 and CD83 and to elicit a synergistic effect, in combination with the chimeric antibodies, especially the IgG4 isotype chimeric antibody, on the expression of CD86 and CD83.

Example 4: Activation Effect of Dendrocyte on CD8 T Cell

After recognizing an external antigen, dendrocytes present a MHC/foreign antigen to T cells. Then, T cells recognize the MHC/foreign antigen and are activated to effectively remove the foreign antigen. In order to examine whether the anti-CD40 antibody provided in the present disclosure induces T cell activation, the Burkitt's lymphoma cell line Ramos was used as a foreign antigen in a T cell activation assay.

After being cultured in a 10% fetal bovine serum RPMI medium, the Ramos cell line (ATCC®, ATCC CRL-1596) were repetitively frozen and thawed twice and centrifuged. Absorbance of the supernatant (Ramos lysate) thus obtained was measured at 280 nm and arbitrarily set in the concentration unit "mg/mL".

Dendrocytes which were differentiated from $5\times10^5$ monocytes as described in Example 3-1 were seeded at a density of $5\times10^5$ cells/well into 12-well culture dishes to which the prepared Ramos lysate was then added at a concentration of 20 μg/mL. For comparison of effects of the anti-CD40 antibodies, the cells were incubated with 10 μg/mL of each of the three chimeric 5C2 antibodies (chimeric IgG1, chimeric IgG2, and chimeric IgG4) and the CP870,893 analogue (U.S. Pat. No. 7,338,660 B2; 21.4.1 antibody; refer to Table 3). On the next day, PBMC (peripheral blood mononuclear cell) was separated from the whole blood from the donor of the dendrocytes and then co-cultured with the prepared dendrocytes.

Dendrocytes were identified by immunostaining with an anti-CD11c antibody-FITC (eBiosceince, Cat. No.: 11-0116-42). Degrees of activation of the dendrocytes were accounted for by expression levels of the co-stimulatory factors CD86 and CD83 which were measured as fluorescence intensities detected after staining the cells with each of anti-CD86 antibody-PE (eBiosceince, Cat. No.: 12-0869-42) and anti-CD83 antibody-APC (eBiosceince, Cat. No.: 17-0839-42).

Figure 14:
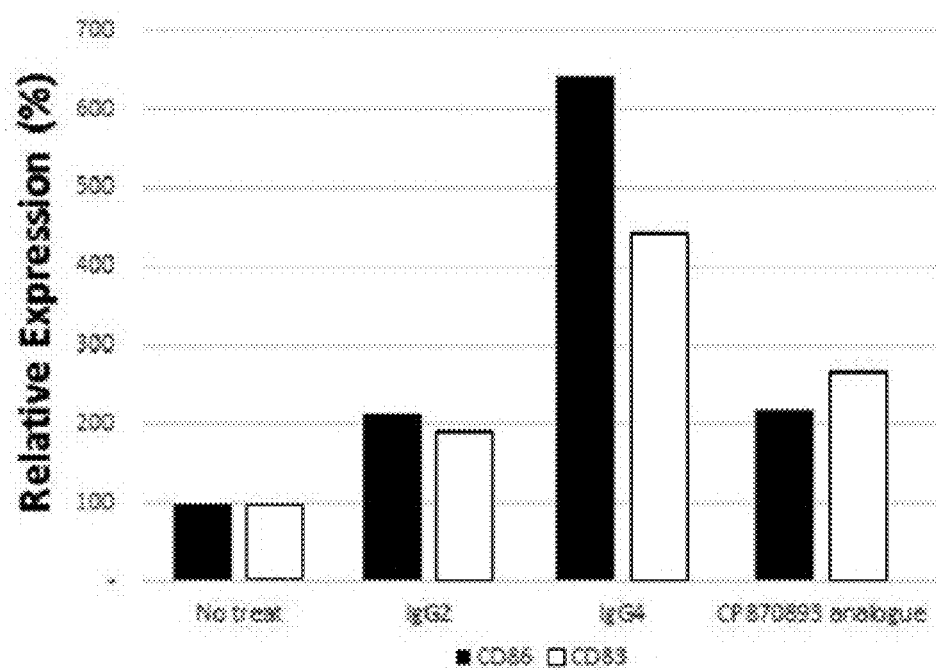
FIG. 14 is a graph showing the expression level of CD86 and CD83 in dendrocytes which are treated with human IgG2 chimeric antibody (chimeric IgG2) or human IgG4 chimeric antibody (chimeric IgG4) of monoclonal antibody 5C2 and co-cultured with PBMC, wherein the expression level is indicated as a relative value to that of a control group (no treat: antibody-untreated group).

The fluorescence intensities obtained above are depicted as relative values to a control (not treated with the antibody, 100%) in FIG. 14 (No treat: treated with no antibodies, IgG2: treated with IgG2 chimeric antibody, IgG4: treated with IgG4 chimeric antibody, CP870893: treated with CP870,893 analogue). When co-cultured with PBMC, dendrocytes increased in the expression levels of CD86 and CD83 in the presence of the chimeric antibodies of the monoclonal antibody 5C2 and a remarkable increase was observed particularly in the presence of the IgG4 chimeric antibody.

Figure 15:
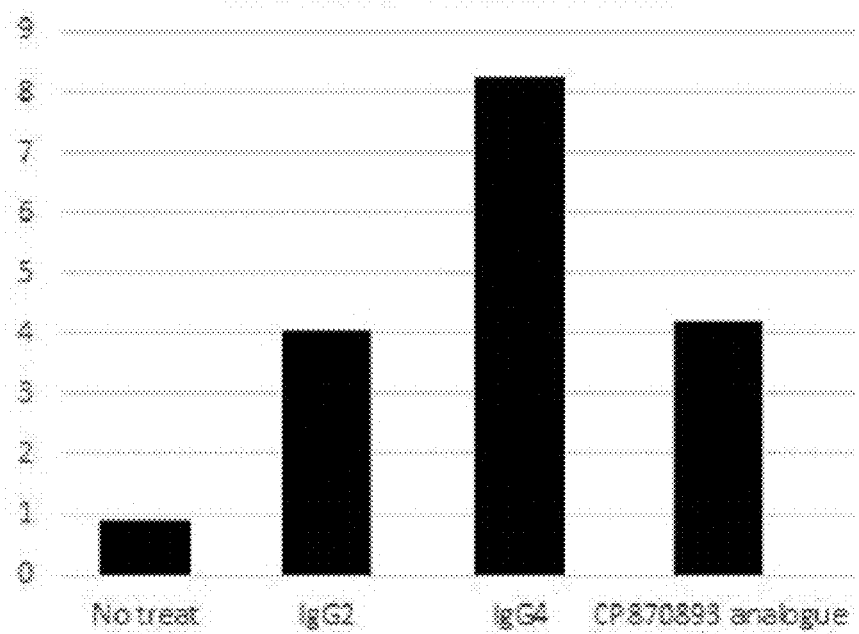
FIG. 15 is a graph showing the ratio (%) of activated CD69-positive CD8 cells in dendrocytes which are treated with human IgG2 chimeric antibody (chimeric IgG2) or human IgG4 chimeric antibody (chimeric IgG4) of monoclonal antibody 5C2 and co-cultured with PBMC, wherein the expression level is indicated as a relative value to that of a control group (no treat: antibody-untreated group).

For T cell activation assay, PBMC co-cultured with dendrocytes were treated with the antibodies and immunostained with anti-CD8-FITC (Dinona, Cat. No.: 10143B) and anti-CD69-PE (eBioscience, Cat. No.: 12-0699-42) together. CD8-expressing cells (CD8-FITC positive cells) and CD69-expressing cells (CD69 positive cells) were selected with reference to the fluorescence intensities detected. Proportions (% based on numbers of cells) of CD69-positive cells in the selected CD8-FITC positive T cell population are depicted in FIG. 15. As shown in FIG. 15, proportions of activated CD69-positive CD8 cells increased with the application of the chimeric antibodies of the monoclonal antibody 5C2. Particularly, the proportion of activated CD69-positive CD8 was observed to peak upon treatment with the IgG4 chimeric antibody.

Figure 16:
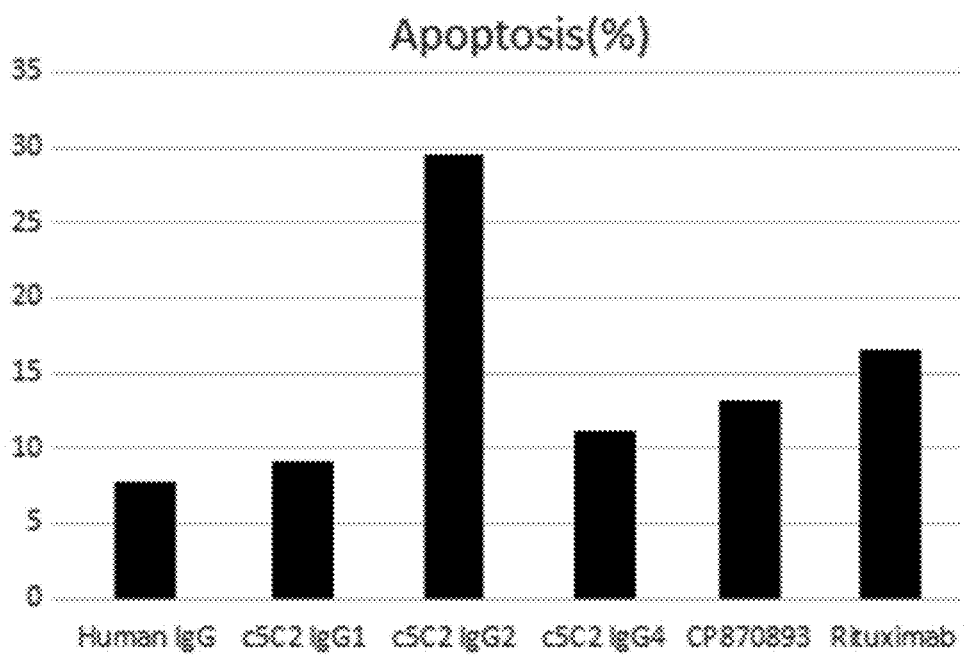
FIG. 16 is a graph showing Ramos tumor cell line apoptosis efficacy (%) induced by chimeric 5C2 antibodies (Human IgG1: irrelevant human IgG1; c5C2 IgG1: IgG1: chimeric 5C2 antibody comprising human IgG1 constant region; c5C2 IgG2: chimeric 5C2 antibody comprising human IgG2 constant region; c5C2: chimeric 5C2 antibody comprising human IgG4 constant region; CP870,893: a control antibody; Rituximab: a control antibody).

Example 5: Assay for Apoptotic Efficacy 5-1. Assay for Apoptotic Effect of Chimeric 5C2 Antibody In order to identify the direct cytotoxicity of the 5C2 antibody against tumor cell lines, an apoptosis test was conducted. The Ramos cell line (ATCC®, ATCC CRL-1596) was washed with phosphate buffered saline, resuspended in a 5.0% fetal bovine serum-supplemented RPMI, and plated at a density of $2 \times 10^5$ cells/well into microplates. The cells were incubated with 1.0 μg/mL of each of the three anti-CD40 chimeric antibodies (IgG1, IgG2, and IgG4), the CP870,893 analogue, and Rituxan at 37° C. for 2 days in a 5% $CO_2$ atmosphere. Cytotoxicity effects were determined by positive cell proportions (%) after staining FITC Annexin-V (BD Pharmingen, Cat. No.: 51-65874X) and 7-AAD (BD Pharmingen, Cat. No.: 51-68981E) according to the manufacturer's instruction. The test results are depicted in FIG. 16. As can be seen in FIG. 16, the 5C2 IgG2 isotype exhibited excellent anti-tumor cytotoxicity.

Figure 17:
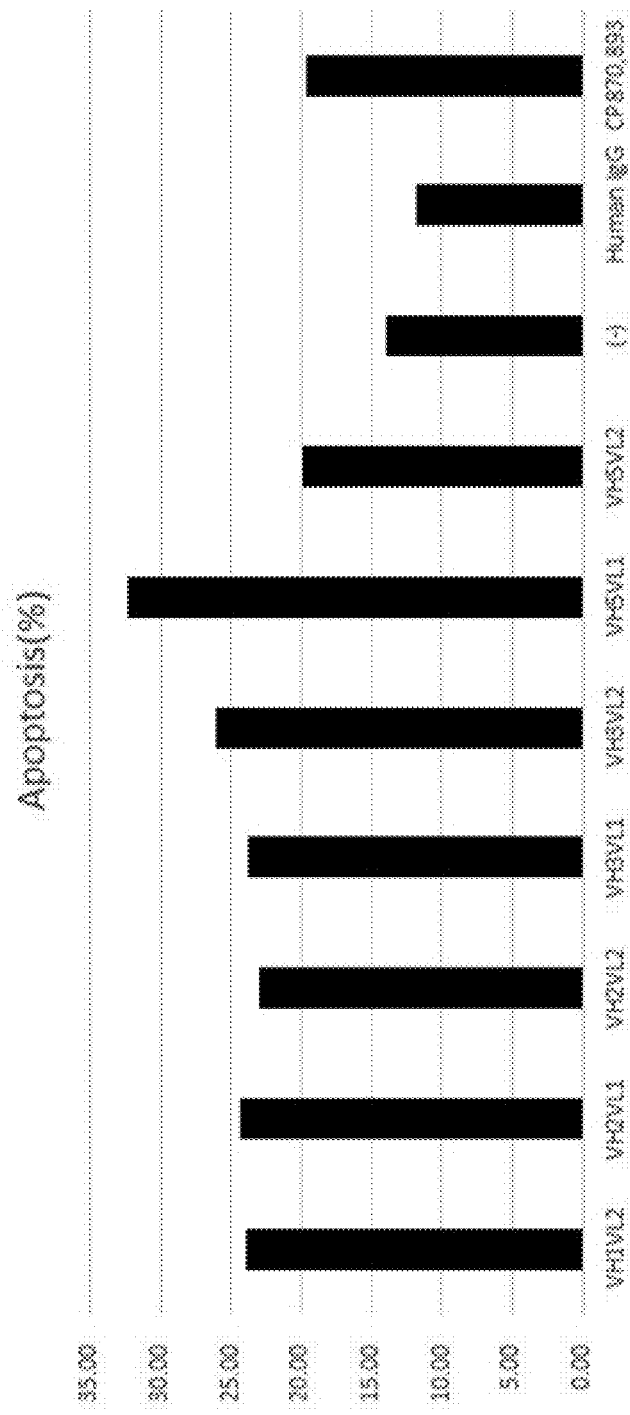
FIG. 17 is a graph showing Raji tumor cell line apoptosis efficacy (%) induced by humanized 5C2 antibodies (7 humanized 5C2 antibodies, VH1VL2, VH2VL1, VH2VL2, VH3VL1, VH3VL2, VH5VL1, VH5VL2; (−): antibody-untreated group; Human IgG: irrelevant human IgG1; CP870,893: a control antibody).

For use in examining the apoptotic efficacy of humanized antibody 5C2, the Raji Burkitt's lymphoma cell line (ATCC®, ATCC CCL-86) was washed with phosphate buffered saline, resuspended in a 3.0% fetal bovine serum-supplemented RPMI medium, and plated at a density of $2 \times 10^5$ cells/well into microplates. The cells were incubated with 10.0 μg/mL of each of seven humanized antibodies 5C2 IgG2 (VH1VL2, VH2VL1, VH2VL2, VH3VL1, VH3VL2, VH5VL1, and VH5VL2), the CP870,893 analogue, and the human IgG at 37° C. for two days in a 5% $CO_2$ atmosphere. Subsequently, as described in Example 5-1, the cells were stained with FITC Annexin-V and 7-AAD to determine the apoptotic effect. The result is depicted in FIG. 17. As shown in FIG. 17, all the seven humanized antibodies were found to have higher apoptotic effects than the CP870,893 analogue.

Example 6: T Cell Activation by 5C2 Antibody in Presence of Super-Antigen Staphylococcal Enterotoxin B (SEB)

Because T cell activation is made in an antigen-specific manner, one antigen cannot induce the activation unless T cells have the same TCR. A super-antigen, such as SEB, which can activate T cells in a non-specific manner, should be employed in order to generally activate T cells in in vitro tests using PBMC.

In this test, SEB was applied to PBMC to establish a condition for T cell activation before examining whether treatment with 5C2 antibodies further enhanced an immune reaction.

Figure 18:
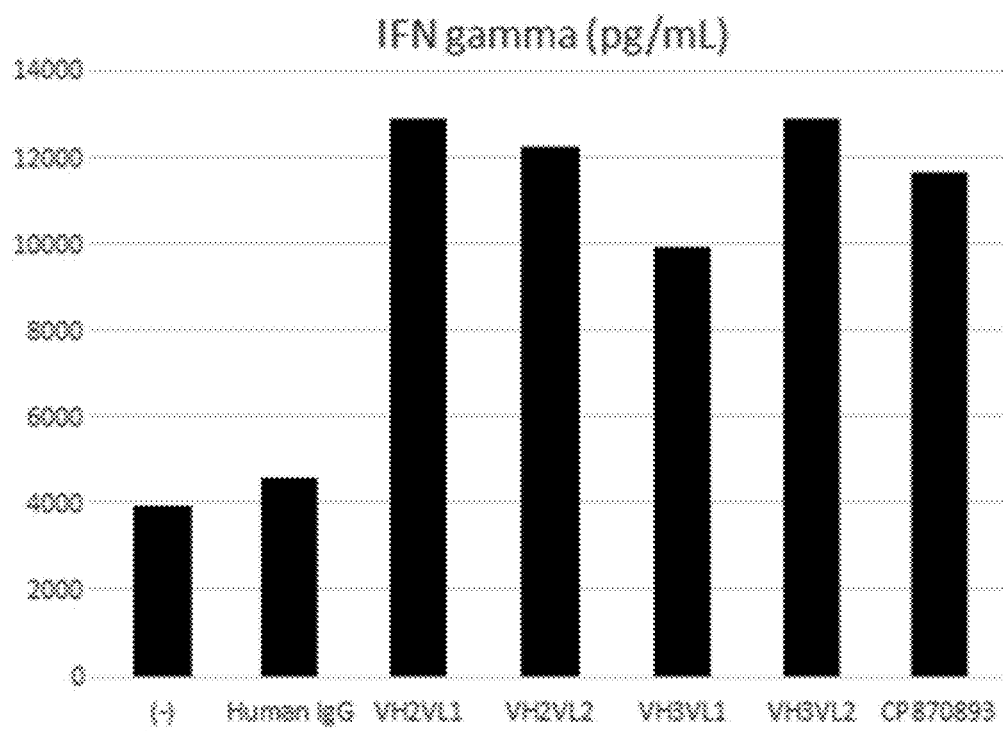
FIG. 18 is a graph showing T-cell activation level by 5C2 antibody under super-antigen SEB condition, wherein the T-cell activation level was obtained by treating PBMC with 30 ng/mL of SEB (Staphylococcal Enterotoxin B), to non-specifically induce T-cell activation, followed by treating with each of humanized 5C2 antibodies, and then, measuring the amount of IFN-gamma which is secreted by the treatment of humanized 5C2 antibodies (4 humanized 5C2 antibodies; (−): antibody-untreated group; Human IgG: irrelevant human IgG1; CP870,893: a control antibody).

After being isolated from the whole blood, from a healthy volunteer, PBMC was seeded at a density of $1 \times 10^6$ cells/well into microplates. Then, the cells were treated with 30 ng/mL of SEB, together with 10 μg/mL of each of five humanized antibodies 5C2 (VH2VL1, VH2VL2, VH3VL1, and VH3VL2), the CP870,893 analogue, and the human IgG at 37° C. for three days in a 5% $CO_2$ atmosphere. The medium supernatant was taken and used to measure an amount of human IFN-gamma (Affymetrix, Cat. NO.: 88-7316-22) according to the manufacturer's instruction. The result thus obtained is depicted in FIG. 18. As can be seen FIG. 18, the amount of IFN-gamma produced upon treatment with the 5C2 humanized antibodies was two or three times larger than with the control, implying that 5C2 stimulation can further enhance an immune response.

Example 7: Assay for Anti-Tumor Effect of 5C2 in Animal Model

Being able to introduce CD8 T cell activation via dendrocytes, the 5C2 antibodies are expected to have an anti-tumor effector. In addition, the apoptotic effect of the 5C2 antibodies on CD40-expressing tumor cell lines allows the anticipation of an anti-tumor effector accompanied.

The 5C2 antibodies have no cross reactivity to mouse CD40. Thus, effects of the 5C2 antibodies were tested in two models: injected with a tumor cell line alone and in combination with human dendrocytes and peripheral blood mononuclear cell (PBMC).

The leukemia cell line Ramos (ATCC®, ATCC CRL-1596) was subcutaneously injected alone or human dendrocytes and PBMC to NSG (NOD.Cg-Prkdcscidll2rgtm1Wjl/SzJ) mice (the Jackson Laboratory, 25 grams, 6-8 weeks old).

In this test, dendrocytes were prepared by taking whole blood from a healthy adult volunteer, separating PBMC from the whole blood with the aid of FICOLL® PAQUE PLUS (GE Healthcare, Cat. No.: 17-1440-03), and differentiating the adherent cells in the presence of rhGM-CSF (Recombinant Human Granulocyte Macrophage Colony Stimulating Factor; JW creagene) and rhIL-4 (JW creagene), as in Example 3-1. On day 7 of differentiation, dendrocytes were detached, washed with phosphate buffered saline, and subcutaneously injected at a density of $5 \times 10^5$ cells/mouse to the mouse abdomen.

After being prepared by separation from whole blood taken from the same donor of dendrocytes, with the aid of FICOLL® PAQUE PLUS (GE Healthcare, Cat. No.: 17-1440-03), PBMC was washed with phosphate buffered saline and subcutaneously injected at a density of $2 \times 10^6$ cells/mouse to the mouse abdomen.

Subsequent to the cell injection, the chimeric 5C2 IgG2 antibody or phosphate buffered saline was intraperitoneally injected. At the time of one week later, the antibody or phosphate buffered saline was further injected once. The assay procedure is summarized in Table 7, below:

TABLE 7

Assay for Anti-Tumor Effector of 5C2 in Animal

| Group | | Tumor | | Effector | | | Drug | | |
|---|---|---|---|---|---|---|---|---|---|
| Group | N | Tumor | Number Route | Type | Number | Route | Type | Dose (mg/Kg) | # of Dose Route |
| Group 1 | 5 | Ramos | 1 × 10⁷ S.C. | None | NA | S.C. | PBS | NA | 2 I.P. |
| Group 2 | 5 | | | None | NA | | 5C2 | 1.0 | |
| Group 3 | 5 | | | DC/PBMC | 5 × 10⁵/2 × 10⁶ | | PBS | NA | |
| Group 4 | 5 | | | DC/PBMC | 5 × 10⁵/2 × 10⁶ | | 5C2 | 1.0 | |

After antibody administration, tumor volumes (mm³) were monitored.

Figure 19:
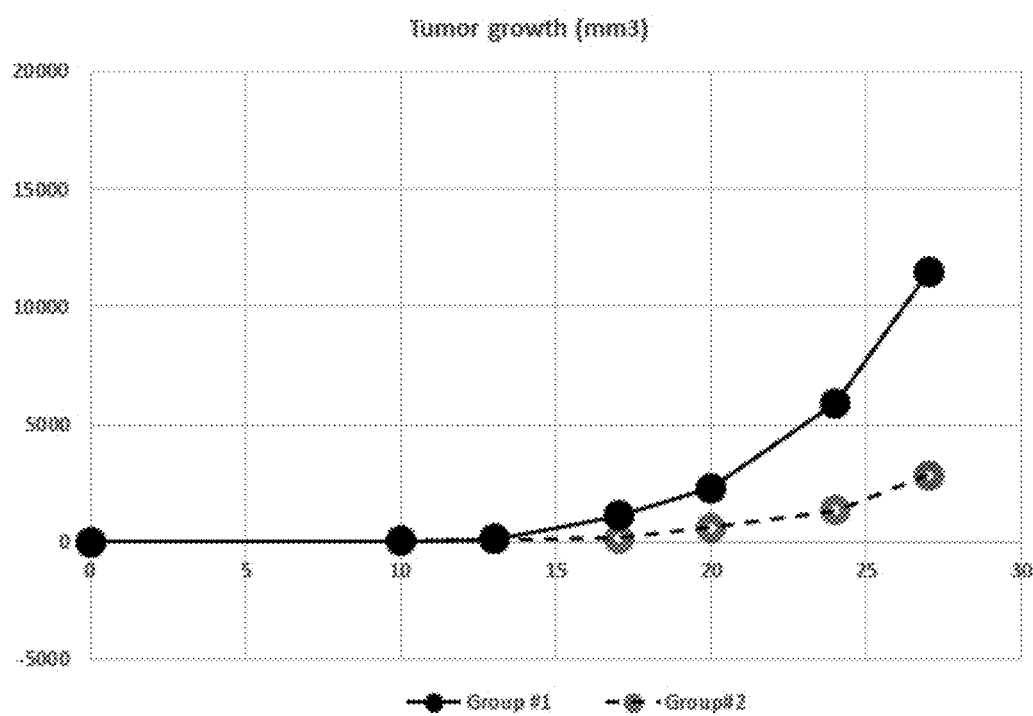
FIG. 19 is a graph showing the change in tumor volume in xenograft mice models when they are treated with chimeric 5C2 IgG2 antibody alone, wherein the results are shown according to the number of days after antibody injection.
Figure 20:
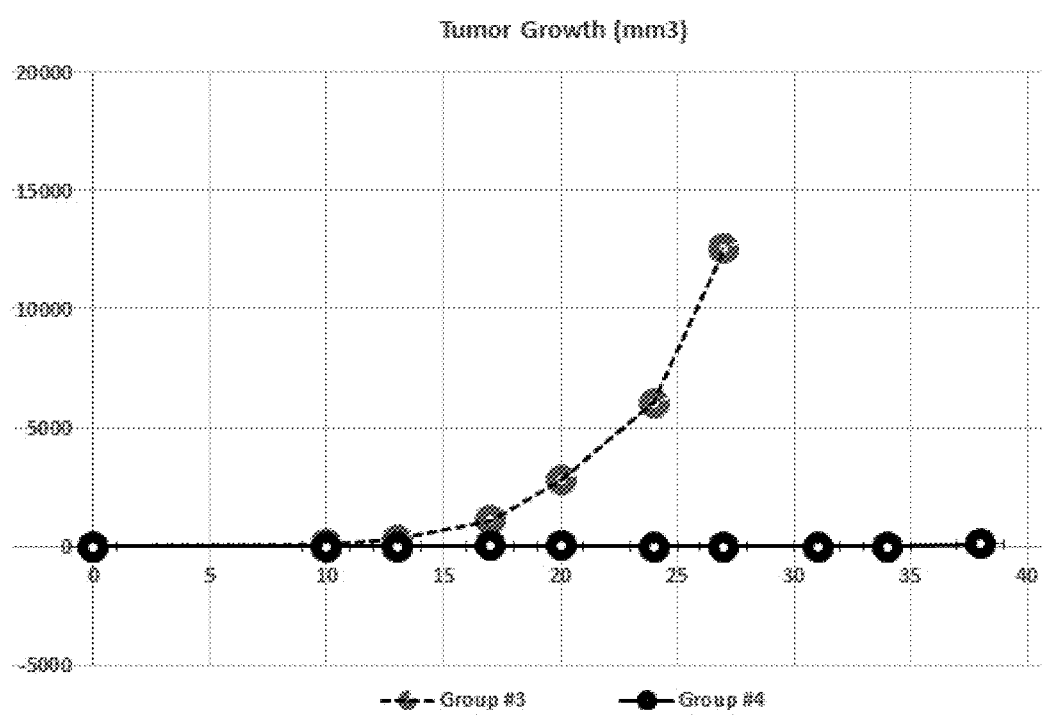
FIG. 20 is a graph showing the change in tumor volume in xenograft mice models co-grafted with human dendrocyte and PBMC when they are treated with chimeric 5C2 IgG2 antibody, wherein the results are shown according to the number of days after antibody injection.

Average values of the tumor volumes (mm³) that has changed with time are given in Table 8 and depicted in FIGS. 19 and 20.

TABLE 8

Average Tumor Volume (mm³)

| Time after Ab administ. (Day) | 0 | 10 | 13 | 17 | 20 | 24 | 27 | 31 | 34 | 38 |
|---|---|---|---|---|---|---|---|---|---|---|
| Group 1 | 0 | 24.1 | 105.6 | 1090.0 | 2287.2 | 5912.3 | 11481.9 | — | — | — |
| Group 2 | 0 | 44.5 | 111.0 | 141.2 | 591.5 | 1347.6 | 2816.7 | — | — | — |
| Group 3 | 0 | 110.9 | 308.4 | 1109.0 | 2786.2 | 6073.3 | 12537.8 | — | — | — |
| Group 4 | 0 | 2.8 | 5.2 | 23.2 | 38.4 | 0 | 0 | 0 | 0 | 96.2 |

As shown in Table 8 and FIG. 19, the 5C2 antibody exhibited the effect of delaying the growth of tumor in the animal model injected with tumor cells alone (Group 2). The apoptotic effect of the 5C2 antibody seems to contribute to the anti-tumor effect. In the animal model injected with the tumor cells together with dendrocytes and PBMC, as is understood from Table 8 and FIG. 20, the tumor rapidly grew to over 10,000 mm³ after 24 days for the control, but the tumor growth was perfectly suppressed until 34 days after administration of the 5C2 antibody (Group 4). After 34 days, tumor growth was observed in one mouse because the lives of the injected human dendrocytes and PBMC came to an end in the inventors' opinion.

---

The invention claimed is:

1. An anti-CD40 antibody or an antigen-binding fragment thereof, comprising the following complementarity determining region (CDRs):
- CDR-H1 comprising the amino acid sequence of SEQ ID NO: 17 or SEQ ID NO: 33,
- CDR-H2 comprising the amino acid sequence of SEQ ID NO: 18 or SEQ ID NO: 34,
- CDR-H3 comprising the amino acid sequence of SEQ ID NO: 19,
- CDR-L1 comprising the amino acid sequence of SEQ ID NO: 20 or SEQ ID NO: 35,
- CDR-L2 comprising the amino acid sequence of SEQ ID NO: 21 or SEQ ID NO: 36, and
- CDR-L3 comprising the amino acid sequence of SEQ ID NO: 22.

2. The anti-CD40 antibody or the antigen-binding fragment thereof according to claim 1, comprising:
- a heavy-chain variable region comprising the amino acid sequence of SEQ ID NO: 1, 23, 24, 25, 26, 27, or 28; and
- a light-chain variable region comprising the amino acid sequence of SEQ ID NO: 3, 29, or 30.

3. The anti-CD40 antibody or the antigen-binding fragment thereof according to claim 1, wherein the anti-CD40 antibody is an animal antibody, a chimeric antibody, or a humanized antibody.

4. The anti-CD40 antibody or the antigen-binding fragment thereof according to claim 1, wherein the antigen-binding fragment is scFv, (scFv)2, Fab, Fab', or F(ab')2 of the anti-CD40 antibody.

5. The anti-CD40 antibody or the antigen-binding fragment thereof according to claim 1, having an agonist activity for CD40.

6. A pharmaceutical composition comprising the anti-CD40 antibody or the antigen-binding fragment thereof according to claim 1.

7. A nucleic acid encoding the anti-CD40 antibody or the antigen-binding fragment thereof according to claim 1.

8. The nucleic acid according to claim 7, encoding either or both of:
- an amino acid sequence comprising SEQ ID NO: 17 or SEQ ID NO: 33, and SEQ ID NO: 18 or SEQ ID NO: 34, and SEQ ID NO: 19; and
- an amino acid sequence comprising SEQ ID NO: 20 or SEQ ID NO: 35, and SEQ ID NO: 21 or SEQ ID NO: 36, and SEQ ID NO: 22.

9. The nucleic acid of claim 7, encoding either or both of:
- the amino acid sequence of SEQ ID NO: 1, 23, 24, 25, 26, 27, or 28; and
- the amino acid sequence of SEQ ID NO: 3, 29, or 30.

10. A recombinant vector comprising the nucleic acid of claim 8.

11. A recombinant cell comprising the recombinant vector of claim 10.

12. An anti-CD40 antibody or an antigen-binding fragment thereof, which comprise CDR-H1, CDR-H2, CDR-H3, CDR-L1, CDR-L2, and CDR-L3 of an anti-CD40 antibody produced by the hybridoma of accession number KCLRF-BP-00381.

13. The anti-CD40 antibody or an antigen-binding fragment thereof according to claim 12, which comprise a heavy chain variable region and a light chain variable region of an anti-CD40 antibody produced by the hybridoma of accession number KCLRF-BP-00381.

14. The anti-CD40 antibody or an antigen-binding fragment thereof according to claim 12, wherein the anti-CD40 antibody is produced by the hybridoma of accession number KCLRF-BP-00381.

15. A hybridoma, deposited with accession number KCLRF-BP-00381, for producing an anti-CD40 antibody.

16. A method of treating a disease, the method comprising administering the anti-CD40 antibody or the antigen-binding fragment thereof according to claim 1 to a subject in need of treating the disease, wherein the disease is selected from the group consisting of cancer and cancer metastasis.

17. The method of claim 16, wherein the anti-CD40 antibody or the antigen-binding fragment thereof comprises:
- a heavy-chain variable region comprising the amino acid sequence of SEQ ID NO: 1, 23, 24, 25, 26, 27, or 28; and
- a light-chain variable region comprising the amino acid sequence of SEQ ID NO: 3, 29, or 30.

18. A method of treating a disease, the method comprising administering an anti-CD40 antibody or an antigen-binding fragment thereof to a subject in need of treating the disease, wherein the disease is selected from the group consisting of cancer and cancer metastasis, wherein the anti-CD40 antibody is selected from the group consisting of:
- an anti-CD40 antibody produced by hybridoma of accession number KCLRF-BP-00381, or an antigen-binding fragment thereof;
- an anti-CD40 antibody comprising CDR-H1, CDR-H2, CDR-H3, CDR-L1, CDR-L2, and CDR-L3 of the anti-CD40 antibody produced by the hybridoma of accession number KCLRF-BP-00381, or an antigen-binding fragment thereof;
- and an anti-CD40 antibody comprising the heavy-chain and light-chain variable regions of the anti-CD40 antibody produced by the hybridoma of accession number KCLRF-BP-00381, or an antigen-binding fragment thereof.

* * * * *

SEQUENCE LISTING

```
<160> NUMBER OF SEQ ID NOS: 36

<210> SEQ ID NO 1
<211> LENGTH: 116
<212> TYPE: PRT
<213> ORGANISM: Artificial Sequence
<220> FEATURE:
<223> OTHER INFORMATION: Synthetic_Heavy chain variable region of mouse
      anti-CD40 5C2

<400> SEQUENCE: 1

Gln Val Gln Met Leu Gln Ser Gly Thr Glu Leu Val Arg Pro Gly Thr
1               5                   10                  15

Ser Val Lys Val Ser Cys Lys Ala Ser Gly Tyr Gly Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Tyr Gly Gly Val Asn Tyr Asn Glu Lys Phe
    50                  55                  60

Lys Gly Lys Ala Ile Leu Thr Ala Asp Lys Ser Ser Ser Thr Ala Tyr
65                  70                  75                  80

Met His Leu Thr Ser Leu Thr Ser Asp Asp Ser Ala Val Tyr Phe Cys
                85                  90                  95
```

Ala Arg Gly Gly Ser Gly Phe Ala Phe Trp Gly Gln Gly Thr Leu Val
            100                 105                 110

Thr Val Ser Thr
        115

<210> SEQ ID NO 2
<211> LENGTH: 348
<212> TYPE: DNA
<213> ORGANISM: Artificial Sequence
<220> FEATURE:
<223> OTHER INFORMATION: Synthetic_DNA encoding heavy chain variable
      region of mouse anti-CD40 5C2

<400> SEQUENCE: 2
caggtacaga tgctgcagag cggaactgaa ctggttagac ctggtactag cgttaaggtc     60
agctgtaagg ctagcggata cggtttcacc aactacctga tcgaatgggt caagcagagg    120
ccaggacaag gtttggagtg gattggagtg attaacccg ggtatggggg cgtgaattac     180
aatgagaagt ttaaaggcaa agccatactg accgcagaca atcaagtag taccgcctat     240 atgcacctga catctttgac atctgacgat tctgccgtgt attttgcgc ccggggcggg     300 agtggctttg ctttttgggg ccagggcaca cttgtgactg tgtctaca               348

<210> SEQ ID NO 3
<211> LENGTH: 107
<212> TYPE: PRT
<213> ORGANISM: Artificial Sequence
<220> FEATURE:
<223> OTHER INFORMATION: Synthetic_Light chain variable region of mouse
      anti-CD40 5C2

<400> SEQUENCE: 3

Asp Ile Gln Met Thr Gln Thr Thr Ser Ser Leu Ser Ala Ser Leu Gly
1               5                   10                  15

Gln Arg Val Thr Ile Ser Cys Arg Ala Ser Gln Asp Ile Ser Asn His
            20                  25                  30

Leu Asn Trp Tyr Gln Gln Lys Pro Asn Gly Thr Val Arg Leu Leu Ile
        35                  40                  45

Ser Ser Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 4
<211> LENGTH: 321
<212> TYPE: DNA
<213> ORGANISM: Artificial Sequence
<220> FEATURE:
<223> OTHER INFORMATION: Synthetic_DNA encoding light chain variable
      region of mouse anti-CD40 5C2

<400> SEQUENCE: 4
gacatccaaa tgacccaaac cacctcctca ctttccgcat ctcttggaca aagagtcacc     60
atctcctgta gggcaagtca agacatctcc aaccacctca actggtacca gcagaagcca    120
aacggaactg ttaggttgtt gatctccagc acctcacgtt tgcactcagg agtaccatca    180

```
cgattcagcg gtagtggttc tggtacagat tacagcttga ccattagcaa cctggagcag    240
gaggatattg ctacctactt ctgccagcag ggcaataccc tgccttggac atttgggggg    300
ggcacaaaac tggaaattaa g                                              321
```

<210> SEQ ID NO 5
<211> LENGTH: 446
<212> TYPE: PRT
<213> ORGANISM: Artificial Sequence
<220> FEATURE:
<223> OTHER INFORMATION: Synthetic_Heavy chain of IgG1 chimeric anti-CD40 antibody 5C2

<400> SEQUENCE: 5

```
Gln Val Gln Met Leu Gln Ser Gly Thr Glu Leu Val Arg Pro Gly Thr
1               5                   10                  15

Ser Val Lys Val Ser Cys Lys Ala Ser Gly Tyr Gly Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Tyr Gly Gly Val Asn Tyr Asn Glu Lys Phe
    50                  55                  60

Lys Gly Lys Ala Ile Leu Thr Ala Asp Lys Ser Ser Thr Ala Tyr
65                  70                  75                  80

Met His Leu Thr Ser Leu Thr Ser Asp Asp Ser Ala Val Tyr Phe Cys
                85                  90                  95

Ala Arg Gly Gly Ser Gly Phe Ala Phe Trp Gly Gln Gly Thr Leu Val
            100                 105                 110

Thr Val Ser Thr Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335
```

```
Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 6
<211> LENGTH: 1341
<212> TYPE: DNA
<213> ORGANISM: Artificial Sequence
<220> FEATURE:
<223> OTHER INFORMATION: Synthetic_DNA encoding heavy chain of IgG1
      chimeric anti-CD40 antibody 5C2

<400> SEQUENCE: 6
caggtacaga tgctgcagag cggaactgaa ctggttagac ctggtactag cgttaaggtc      60
agctgtaagg ctagcggata cggtttcacc aactacctga tcgaatgggt caagcagagg     120
ccaggacaag gtttggagtg gattggagtg attaaccccg gtatgggggg cgtgaattac     180
aatgagaagt ttaaaggcaa agccatactg accgcagaca atcaagtag taccgcctat     240 atgcacctga catctttgac atctgacgat tctgccgtgt attttttgcgc ccggggcggg     300 agtggctttg cttttttgggg ccagggcaca cttgtgactg tgtctacagc ttcaactaag     360
ggaccaagcg tattcccact tgctccatct agcaagagca ctagcggagg aacagctgct     420
ttggggtgtt tggtaaagga ttactttccc gaacctgtta ccgtgagctg aacagcgggg     480
gctttgacaa gtggcgttca tacatttcct gccgttttgc aaagcagcgg cttgtatagc     540
ttgagctctg ttgttaccgt tccaagctca tctctgggca cacaaacata catctgcaac     600
gtgaaccaca gccctcaaa caccaaggtg gacaagaagg tggagccaaa gtcttgcgac     660
aagacccaca cctgtccacc ttgtccagcc cctgaactcc tgggggggccc ttcagtttt      720 ctctttcctc ctaaacctaa agatacactc atgatcagtc ggacccctga gttacctgt      780 gtggtggtcg atgtgtctca tgaagatcct gaagtcaagt taactggta tgtggacggc      840 gtggaggtgc ataatgccaa gaccaagcct cggaggag aatataattc tacctatcgc      900
gtcgtctctg tcctcaccgt cctgcatcag gactggctga atggcaaaga gtataagtgc      960
aaagtcagta acaaagccct ccccgccccc atagagaaaa ccattagtaa agccaaaggg    1020
cagccccgcg agcccaggt ctatacactg cccccccagta gagacgagct gacaaagaat    1080
caggtgtctc tgacatgcct ggtgaaaggc ttttatccct ctgacattgc cgtcgagtgg    1140
gagtctaatg gcagcccga gaataattat aagacaacac cccccgtgct ggacagtgac    1200
ggctcatttt tcctgtattc aaaactgaca gtggacaaaa gtcggtggca gcaggggaat    1260
gtgttttcat gcagtgtcat gcacgaggcc ctccacaatc actataccca gaaatctctg    1320
agtctctctc tgggaaatg a                                              1341
```

-continued

<210> SEQ ID NO 7
<211> LENGTH: 442
<212> TYPE: PRT
<213> ORGANISM: Artificial Sequence
<220> FEATURE:
<223> OTHER INFORMATION: Synthetic_Heavy chain of IgG2 chimeric
      anti-CD40 antibody 5C2

<400> SEQUENCE: 7

```
Gln Val Gln Met Leu Gln Ser Gly Thr Glu Leu Val Arg Pro Gly Thr
1               5                   10                  15

Ser Val Lys Val Ser Cys Lys Ala Ser Gly Tyr Gly Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Tyr Gly Gly Val Asn Tyr Asn Glu Lys Phe
    50                  55                  60

Lys Gly Lys Ala Ile Leu Thr Ala Asp Lys Ser Ser Thr Ala Tyr
65                  70                  75                  80

Met His Leu Thr Ser Leu Thr Ser Asp Asp Ser Ala Val Tyr Phe Cys
                85                  90                  95

Ala Arg Gly Gly Ser Gly Phe Ala Phe Trp Gly Gln Gly Thr Leu Val
            100                 105                 110

Thr Val Ser Thr Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
    210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365
```

Pro Ser Asp Ile Ala Val Glu Trp Glu Ser Asn Gly Gln Pro Glu Asn
        370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
            435                 440

<210> SEQ ID NO 8
<211> LENGTH: 1329
<212> TYPE: DNA
<213> ORGANISM: Artificial Sequence
<220> FEATURE:
<223> OTHER INFORMATION: Synthetic_DNA encoding heavy chain of IgG2
      chimeric anti-CD40 antibody 5C2

<400> SEQUENCE: 8

```
caggtacaga tgctgcagag cggaactgaa ctggttagac ctggtactag cgttaaggtc    60
agctgtaagg ctagcggata cggtttcacc aactacctga tcgaatgggt caagcagagg   120
ccaggacaag gtttggagtg gattggagtg attaaccccg gtatgggggc gtgaattac   180
aatgagaagt ttaaaggcaa agccatactg accgcagaca atcaagtag taccgcctat   240
atgcacctga catctttgac atctgacgat tctgccgtgt attttgcgc cggggcggg   300
agtggctttg cttttggggg ccagggcaca cttgtgactg tgtctacagc ttccaccaag   360
ggcccatccg tgttccctct ggccccatgt tctaggtcta catctgagag caccgccgcc   420
ctcggctgtc tggtgaagga ttatttcccc gagcccgtga ccgtgtcttg aacagcgga   480
gccctgacta gcggagtgca caccttccca gctgtgctgc agagctccgg cctgtacagc   540
ctctcttctg tggtgaccgt gccctctagc aacttcggaa cacagaccta cacatgtaac   600
gtggatcaca gccttccaa caccaaggtg gataagaccg tggagagaaa gtgctgtgtg   660
gagtgccctc catgtcctgc cccacctgtg gctggacctt ctgtgtttct gttccctcca   720
aagccaaagg atacgctgat gatcagcaga actcctgagg tgacctgtgt ggtggtggac   780
gtgagccacg aggatcctga ggtgcagttt aactggtacg tggatggcgt ggaggtgcat   840
aacgctaaga caaagcctag ggaggagcag tttaacagca ccttcagagt ggtgagcgtg   900
ctgaccgtgg tgcaccagga ttggctgaac ggcaaggagt ataagtgtaa ggtgtctaac   960
aagggcctgc cagcccctat tgagaagacc atcagtaaga ccaagggaca gcctagggag  1020
cctcaggtgt acaccctgcc tccttccaga gaggagatga caagaaacca ggtgagcctg  1080
acctgtctgg tgaagggctt ctacccctagc gatatcgccg tggagtggga gagcaacggc  1140
cagcctgaga caactacaa gaccaccca cctatgctgg acagcgatgg ctcttctttc  1200
ctgtactcta agctgaccgt ggacaagagc agatggcagc agggcaacgt gttttcttgt  1260
tctgtgatgc acgaggccct gcacaaccac tacacccaga gtctctgtc tctgtctcca  1320
ggcaagtga                                                          1329
```

<210> SEQ ID NO 9
<211> LENGTH: 443
<212> TYPE: PRT
<213> ORGANISM: Artificial Sequence
<220> FEATURE:

<223> OTHER INFORMATION: Synthetic_Heavy chain of IgG4 chimeric anti-CD40 antibody 5C2

<400> SEQUENCE: 9

```
Gln Val Gln Met Leu Gln Ser Gly Thr Glu Leu Val Arg Pro Gly Thr
1               5                   10                  15

Ser Val Lys Val Ser Cys Lys Ala Ser Gly Tyr Gly Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Tyr Gly Gly Val Asn Tyr Asn Glu Lys Phe
    50                  55                  60

Lys Gly Lys Ala Ile Leu Thr Ala Asp Lys Ser Ser Thr Ala Tyr
65                  70                  75                  80

Met His Leu Thr Ser Leu Thr Ser Asp Asp Ser Ala Val Tyr Phe Cys
                85                  90                  95

Ala Arg Gly Gly Ser Gly Phe Ala Phe Trp Gly Gln Gly Thr Leu Val
            100                 105                 110

Thr Val Ser Thr Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Asp Val Ser Gln Glu Asp Pro Glu Val Gln Phe Asn
                260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400
```

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 10
<211> LENGTH: 1332
<212> TYPE: DNA
<213> ORGANISM: Artificial Sequence
<220> FEATURE:
<223> OTHER INFORMATION: Synthetic_DNA encoding heavy chain of IgG4
      chimeric anti-CD40 antibody 5C2

<400> SEQUENCE: 10

```
caggtacaga tgctgcagag cggaactgaa ctggttagac ctggtactag cgttaaggtc      60
agctgtaagg ctagcggata cggtttcacc aactacctga tcgaatgggt caagcagagg     120
ccaggacaag gtttggagtg gattggagtg attaaccccg gtatggggg cgtgaattac     180
aatgagaagt ttaaaggcaa agccatactg accgcagaca atcaagtag taccgcctat     240
atgcacctga catctttgac atctgacgat tctgccgtgt attttttgcgc ccggggcggg     300
agtggctttg cttttttgggg ccagggcaca cttgtgactg tgtctacagc ttccaccaag     360
ggccccctccg tgttccctct cgccccttgc tccagatcca cctccgagtc taccgccgct     420
ctgggctgcc tggtcaagga ctacttcccc gagcctgtga ccgtgtcttg gaactctggc     480
gcactgacca gcggcgtgca caccttccct gccgtgctgc agtcctccgg cctgtactcc     540
ctgtcctccg tcgtgaccgt gccctcctcc agcctgggca ccaagaccta cacctgtaac     600
gtggaccaca gccctccaa caccaaggtg gacaagcggg tggaatctaa gtacggccct     660
cccctgcccc cctgccctgc ccctgaattt ctgggcggac cttccgtgtt cctgttcccc     720
ccaaagccca aggacaccct gatgatctcc cggacccccg aagtgacctg cgtggtggtg     780
gacgtgtccc aggaagatcc cgaggtccag ttcaattggt acgtggacgg cgtggaagtg     840
cacaacgcca agaccaagcc cagagaggaa cagttcaact ccacctaccg ggtggtgtcc     900
gtgctgaccg tcctgcacca ggactggctg aacggcaaag agtacaagtg caaggtgtcc     960
aacaagggcc tgccctccag catcgaaaag accatctcca aggccaaggg ccagccccgc    1020
gagcctcagg tgtacaccct gccccctagc caggaagaga tgaccaagaa ccaggtgtcc    1080
ctgacctgtc tcgtcaaagg cttctacccc tccgatatcg ccgtggaatg ggagtccaac    1140
ggccagcccg agaacaacta caagaccacc cccctgtgc tggactccga cggctccttc    1200
tttctgtact ctcggctgac cgtggataag agccggtggc aggaaggcaa cgtcttctcc    1260
tgctccgtga tgcacgaggc cctgcacaac cactataccc agaagtccct gtccctgagc    1320
ctgggcaaat ga                                                        1332
```

<210> SEQ ID NO 11
<211> LENGTH: 214
<212> TYPE: PRT
<213> ORGANISM: Artificial Sequence
<220> FEATURE:
<223> OTHER INFORMATION: Synthetic_Light chain of chimeric anti-CD40 5C2

<400> SEQUENCE: 11

Asp Ile Gln Met Thr Gln Thr Thr Ser Ser Leu Ser Ala Ser Leu Gly
1               5                   10                  15

Gln Arg Val Thr Ile Ser Cys Arg Ala Ser Gln Asp Ile Ser Asn His
            20                  25                  30

Leu Asn Trp Tyr Gln Gln Lys Pro Asn Gly Thr Val Arg Leu Leu Ile
        35                  40                  45

Ser Ser Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 645
<212> TYPE: DNA
<213> ORGANISM: Artificial Sequence
<220> FEATURE:
<223> OTHER INFORMATION: Synthetic_DNA encoding light chain of chimeric
      anti-CD40 5C2

<400> SEQUENCE: 12
gacatccaaa tgacccaaac cacctcctca ctttccgcat ctcttggaca aagagtcacc      60
atctcctgta gggcaagtca agacatctcc aaccacctca actggtacca gcagaagcca     120
aacggaactg ttaggttgtt gatctccagc acctcacgtt tgcactcagg agtaccatca     180
cgattcagcg gtagtggttc tggtacagat tacagcttga ccattagcaa cctggagcag     240
gaggatattg ctacctactt ctgccagcag ggcaataccc tgccttggac atttgggggg     300
ggcacaaaac tggaaattaa gcggactgtt gctgctccat ctgtttttat atttcctccc     360
agcgacgagc agctgaaaag cggcactgcc tctgtggtgt gtctgctgaa taatttttac     420 cccgggaag ccaaagtcca gtggaaggtg ataatgccc tccagtctgg aacagtcag     480 gaaagtgtga cagaacagga tagtaaggac tctacttata gcctctcttc tacactgact     540
ctgtcaaagg ccgactatga gaagcataaa gtgtatgcct gcgaggtgac acatcagggc     600
ctgagttcac ccgtgacaaa atcttttaac cgcggcgagt gctga                     645

<210> SEQ ID NO 13
<211> LENGTH: 471
<212> TYPE: PRT
<213> ORGANISM: Artificial Sequence
<220> FEATURE:

<223> OTHER INFORMATION: Synthetic_Heavy chain of humanized anti-CD40 CP870,893

<400> SEQUENCE: 13

```
Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asp Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
        115                 120                 125

Cys Ser Tyr Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Phe Arg Val Val Ser Val Leu Thr Val Val His Gln Asp
                325                 330                 335

Trp Leu Asn Gly Lys Glu Tyr Lys Cys Lys Val Ser Asn Lys Gly Leu
            340                 345                 350

Pro Ala Pro Ile Glu Lys Thr Ile Ser Lys Thr Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400
```

```
Ile Ala Val Glu Trp Glu Ser Asn Gly Gln Pro Glu Asn Asn Tyr Lys
            405                 410                 415

Thr Thr Pro Pro Met Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 14
<211> LENGTH: 1416
<212> TYPE: DNA
<213> ORGANISM: Artificial Sequence
<220> FEATURE:
<223> OTHER INFORMATION: Synthetic_DNA encoding heavy chain of humanized
      anti-CD40 antibody CP870,893

<400> SEQUENCE: 14
atggactgga cctggaggat cctcttcttg gtggcagcag ccacaggagc ccactcccag      60
gtgcagctgg tgcagtctgg ggctgagqtg aagaagcctg gggcctcagt gaaggtctcc    120
tgcaaggctt ctggatacac cttcaccggc tactatatgc actgggtgcg acaggcccct    180
ggacaagggc ttgagtggat gggatggatc aaccctgaca gtggtggcac aaactatgca    240
cagaagtttc agggcagggt caccatgacc agggacacgt ccatcagcac agcctacatg    300
gagctgaaca ggctgagatc tgacgacacg gccgtgtatt actgtgcgag agatcagccc    360
ctaggatatt gtactaatgg tgtatgctcc tactttgact actggggcca gggaaccctg    420
gtcaccgtct cctcagcctc caccaagggc ccatcggtct tccccctggc gccctgctcc    480
aggagcacct ccgagagcac agcggccctg ggctgcctgg tcaaggacta cttccccgaa    540
ccggtgacgg tgtcgtggaa ctcaggcgct ctgaccagcg gcgtgcacac cttcccagct    600
gtcctacagt cctcaggact ctactccctc agcagcgtgg tgaccgtgcc ctccagcaac    660
ttcggcaccc agacctacac ctgcaacgta gatcacaagc ccagcaacac caaggtggac    720
aagacagttg agcgcaaatg ttgtgtcgag tgcccaccgt gcccagcacc acctgtggca    780
ggaccgtcag tcttcctctt ccccccaaaa cccaaggaca ccctcatgat ctcccggacc    840
cctgaggtca cgtgcgtggt ggtggacgtg agccacgaag accccgaggt ccagttcaac    900
tggtacgtgg acggcgtgga ggtgcataat gccaagacaa agccacggga ggagcagttc    960
aacagcacgt tccgtgtggt cagcgtcctc accgttgtgc accaggactg gctgaacggc   1020
aaggagtaca agtgcaaggt ctccaacaaa ggcctcccag cccccatcga gaaaaccatc   1080
tccaaaacca aagggcagcc ccgagaacca caggtgtaca ccctgccccc atcccgggag   1140
gagatgacca agaaccaggt cagcctgacc tgcctggtca aaggcttcta tcccagcgac   1200
atcgccgtgg agtgggagag caatgggcag ccggagaaca actacaagac cacacctccc   1260
atgctggact ccgacggctc cttcttcctc tacagcaagc tcaccgtgga caagagcagg   1320
tggcagcagg ggaacgtctt ctcatgctcc gtgatgcatg aggctctgca caaccactac   1380
acgcagaaga gcctctccct gtctccgggt aaatga                              1416

<210> SEQ ID NO 15
<211> LENGTH: 234
<212> TYPE: PRT
```

<213> ORGANISM: Artificial Sequence
<220> FEATURE:
<223> OTHER INFORMATION: Synthetic_Light chain of humanized anti-CD40
      antibody CP870,893

<400> SEQUENCE: 15

Met Arg Leu Pro Ala Gln Leu Leu Gly Leu Leu Leu Leu Trp Phe Pro
1               5                   10                  15

Gly Ser Arg Cys Asp Ile Gln Met Thr Gln Ser Pro Ser Ser Val Ser
            20                  25                  30

Ala Ser Val Gly Asp Arg Val Thr Ile Thr Cys Arg Ala Ser Gln Gly
        35                  40                  45

Ile Tyr Ser Trp Leu Ala Trp Tyr Gln Gln Lys Pro Gly Lys Ala Pro
    50                  55                  60

Asn Leu Leu Ile Tyr Thr Ala Ser Thr Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ala Asn
            100                 105                 110

Ile Phe Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 16
<211> LENGTH: 705
<212> TYPE: DNA
<213> ORGANISM: Artificial Sequence
<220> FEATURE:
<223> OTHER INFORMATION: Synthetic_DNA encoding light chain of humanized
      anti-CD40 antibody CP870,893

<400> SEQUENCE: 16
atgaggctcc ctgctcagct cctggggctc ctgctgctct ggttcccagg ttccagatgc      60
gacatccaga tgacccagtc tccatcttcc gtgtctgcat ctgtaggaga cagagtcacc     120
atcacttgtc gggcgagtca gggtatttac agctggttag cctggtatca gcagaaacca     180
gggaaagccc ctaacctcct gatctatact gcatccactt tacaaagtgg ggtcccatca     240
aggttcagcg gcagtggatc tgggacagat ttcactctca ccatcagcag cctgcaacct     300
gaagattttg caacttacta ttgtcaacag gctaacattt tcccgctcac tttcggcgga     360
gggaccaagg tggagatcaa acgaactgtg gctgcaccat ctgtcttcat cttcccgcca     420
tctgatgagc agttgaaatc tggaactgcc tctgttgtgt gcctgctgaa taacttctat     480

```
cccagagagg ccaaagtaca gtggaaggtg ataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttag                   705
```

```
<210> SEQ ID NO 17
<211> LENGTH: 8
<212> TYPE: PRT
<213> ORGANISM: Artificial Sequence
<220> FEATURE:
<223> OTHER INFORMATION: Synthetic_CDR-H1 of anti-CD40 antibody

<400> SEQUENCE: 17

Gly Tyr Gly Phe Thr Asn Tyr Leu
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic_CDR-H2 of anti-CD40 antibody

<400> SEQUENCE: 18

Ile Asn Pro Gly Tyr Gly Gly Val
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic_CDR-H3 of anti-CD40 antibody

<400> SEQUENCE: 19

Gly Gly Ser Gly Phe Ala Phe
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic_CDR-L1 of anti-CD40 antibody

<400> SEQUENCE: 20

Gln Asp Ile Ser Asn His
1               5

<210> SEQ ID NO 21
<211> LENGTH: 3
<212> TYPE: PRT
<213> ORGANISM: Artificial Sequence
<220> FEATURE:
<223> OTHER INFORMATION: Synthetic_CDR-L2 of anti-CD40 antibody

<400> SEQUENCE: 21

Ser Thr Ser
1

<210> SEQ ID NO 22
<211> LENGTH: 7
<212> TYPE: PRT
<213> ORGANISM: Artificial Sequence
<220> FEATURE:
```

<223> OTHER INFORMATION: Synthetic_CDR-L3 of anti-CD40 antibody

<400> SEQUENCE: 22

Gln Gln Gly Asn Thr Leu Pro
1               5

<210> SEQ ID NO 23
<211> LENGTH: 116
<212> TYPE: PRT
<213> ORGANISM: Artificial Sequence
<220> FEATURE:
<223> OTHER INFORMATION: Synthetic_heavy chain variable region of
      anti-CD40 antibody

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Gly Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Tyr Gly Gly Val Asn Tyr Asn Glu Lys Phe
50                  55                  60

Lys Gly Arg Ala Thr Leu Thr Ala Asp Lys Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Arg Gly Gly Ser Gly Phe Ala Phe Trp Gly Gln Gly Thr Leu Val
            100                 105                 110

Thr Val Ser Ser
        115

<210> SEQ ID NO 24
<211> LENGTH: 116
<212> TYPE: PRT
<213> ORGANISM: Artificial Sequence
<220> FEATURE:
<223> OTHER INFORMATION: Synthetic_heavy chain variable region of
      anti-CD40 antibody

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Gly Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Tyr Gly Gly Val Asn Tyr Asn Glu Lys Phe
    50                  55                  60

Lys Gly Arg Val Thr Leu Thr Ala Asp Lys Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Arg Gly Gly Ser Gly Phe Ala Phe Trp Gly Gln Gly Thr Leu Val
            100                 105                 110

Thr Val Ser Ser
        115

<210> SEQ ID NO 25

```
<211> LENGTH: 116
<212> TYPE: PRT
<213> ORGANISM: Artificial Sequence
<220> FEATURE:
<223> OTHER INFORMATION: Synthetic_heavy chain variable region of
      anti-CD40 antibody

<400> SEQUENCE: 25

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Gly Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Tyr Gly Gly Val Asn Tyr Asn Glu Lys Phe
    50                  55                  60

Lys Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Gly Ser Gly Phe Ala Phe Trp Gly Gln Gly Thr Leu Val
            100                 105                 110

Thr Val Ser Ser
        115

<210> SEQ ID NO 26
<211> LENGTH: 116
<212> TYPE: PRT
<213> ORGANISM: Artificial Sequence
<220> FEATURE:
<223> OTHER INFORMATION: Synthetic_heavy chain variable region of
      anti-CD40 antibody

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Gly Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Tyr Gly Gly Val Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Gly Ser Gly Phe Ala Phe Trp Gly Gln Gly Thr Leu Val
            100                 105                 110

Thr Val Ser Ser
        115

<210> SEQ ID NO 27
<211> LENGTH: 116
<212> TYPE: PRT
<213> ORGANISM: Artificial Sequence
<220> FEATURE:
<223> OTHER INFORMATION: Synthetic_heavy chain variable region of
      anti-CD40 antibody
```

<400> SEQUENCE: 27

Glu Val Gln Leu Val Gln Ser Gly Ala Glu Val Lys Lys Pro Gly Glu
1               5                   10                  15

Ser Val Lys Ile Ser Cys Lys Ala Ser Gly Tyr Gly Phe Thr Asn Tyr
            20                  25                  30

Leu Ile Glu Trp Val Arg Gln Met Pro Gly Lys Gly Leu Glu Trp Ile
        35                  40                  45

Gly Val Ile Asn Pro Gly Tyr Gly Gly Val Asn Tyr Asn Glu Lys Phe
    50                  55                  60

Lys Gly Gln Ala Thr Leu Ser Ala Asp Lys Ser Ile Ser Thr Ala Tyr
65                  70                  75                  80

Leu Gln Leu Ser Ser Leu Lys Ala Ser Asp Thr Ala Val Tyr Phe Cys
                85                  90                  95

Ala Arg Gly Gly Ser Gly Phe Ala Phe Trp Gly Gln Gly Thr Leu Val
            100                 105                 110

Thr Val Ser Ser
        115

<210> SEQ ID NO 28
<211> LENGTH: 116
<212> TYPE: PRT
<213> ORGANISM: Artificial Sequence
<220> FEATURE:
<223> OTHER INFORMATION: Synthetic_heavy chain variable region of
      anti-CD40 antibody

<400> SEQUENCE: 28

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Gly Phe Thr Asn Tyr
            20                  25                  30

Leu Ile Glu Trp Val Arg Gln Met Pro Gly Lys Gly Leu Glu Trp Ile
        35                  40                  45

Gly Val Ile Asn Pro Gly Tyr Gly Gly Val Asn Tyr Asn Glu Lys Phe
    50                  55                  60

Lys Gly Gln Val Thr Ile Ser Ala Asp Lys Ser Ile Ser Thr Ala Tyr
65                  70                  75                  80

Leu Gln Leu Ser Ser Leu Lys Ala Ser Asp Thr Ala Met Tyr Phe Cys
                85                  90                  95

Ala Arg Gly Gly Ser Gly Phe Ala Phe Trp Gly Gln Gly Thr Leu Val
            100                 105                 110

Thr Val Ser Ser
        115

<210> SEQ ID NO 29
<211> LENGTH: 107
<212> TYPE: PRT
<213> ORGANISM: Artificial Sequence
<220> FEATURE:
<223> OTHER INFORMATION: Synthetic_light chain variable region of
      anti-CD40 antibody

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn His
            20                  25                  30

-continued

```
Leu Asn Trp Tyr Gln Gln Lys Pro Gly Lys Ala Val Lys Leu Leu Ile
         35                  40                  45

Ser Ser Thr Ser Arg Leu His Ser Gly Val Pro Ser Arg Phe Ser Gly
 50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
             85                  90                  95

Thr Phe Gly Gln Gly Thr Lys Val Glu Ile Lys
            100                 105
```

<210> SEQ ID NO 30
<211> LENGTH: 107
<212> TYPE: PRT
<213> ORGANISM: Artificial Sequence
<220> FEATURE:
<223> OTHER INFORMATION: Synthetic_light chain variable region of
      anti-CD40 antibody

<400> SEQUENCE: 30

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Asp Ile Ser Asn His
             20                  25                  30

Leu Asn Trp Tyr Gln Gln Lys Pro Gly Gln Ala Val Arg Leu Leu Ile
         35                  40                  45

Ser Ser Thr Ser Arg Leu His Ser Gly Ile Pro Ala Arg Phe Ser Gly
 50                  55                  60

Ser Gly Ser Gly Thr Glu Tyr Thr Leu Thr Ile Ser Ser Leu Gln Ser
65                  70                  75                  80

Glu Asp Phe Ala Val Tyr Phe Cys Gln Gln Gly Asn Thr Leu Pro Trp
             85                  90                  95

Thr Phe Gly Gln Gly Thr Lys Val Glu Ile Lys
            100                 105
```

<210> SEQ ID NO 31
<211> LENGTH: 149
<212> TYPE: PRT
<213> ORGANISM: Artificial Sequence
<220> FEATURE:
<223> OTHER INFORMATION: Synthetic_Recombinant Human sCD40 Ligand

<400> SEQUENCE: 31

```
Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly
             20                  25                  30

Tyr Tyr Thr Met Ser Asn Asn Leu Val Thr Leu Glu Asn Gly Lys Gln
         35                  40                  45

Leu Thr Val Lys Arg Gln Gly Leu Tyr Tyr Ile Tyr Ala Gln Val Thr
 50                  55                  60

Phe Cys Ser Asn Arg Glu Ala Ser Ser Gln Ala Pro Phe Ile Ala Ser
65                  70                  75                  80

Leu Trp Leu Lys Ser Pro Gly Arg Phe Glu Arg Ile Leu Leu Arg Ala
             85                  90                  95

Ala Asn Thr His Ser Ser Ala Lys Pro Cys Gly Gln Gln Ser Ile His
            100                 105                 110
```

```
Leu Gly Gly Val Phe Glu Leu Gln Pro Gly Ala Ser Val Phe Val Asn
            115                 120                 125

Val Thr Asp Pro Ser Gln Val Ser His Gly Thr Gly Phe Thr Ser Phe
        130                 135                 140

Gly Leu Leu Lys Leu
145

<210> SEQ ID NO 32
<211> LENGTH: 4
<212> TYPE: PRT
<213> ORGANISM: Artificial Sequence
<220> FEATURE:
<223> OTHER INFORMATION: Synthetic_CDR-L2 of anti-CD40 antibody
<220> FEATURE:
<221> NAME/KEY: MOD_RES
<222> LOCATION: (4)
<223> OTHER INFORMATION: Xaa is 1-4 amino acids or absent

<400> SEQUENCE: 32

Ser Thr Ser Xaa
1

<210> SEQ ID NO 33
<211> LENGTH: 5
<212> TYPE: PRT
<213> ORGANISM: Artificial Sequence
<220> FEATURE:
<223> OTHER INFORMATION: Synthetic_CDR-H1 of anti-CD40 antibody

<400> SEQUENCE: 33

Asn Tyr Leu Ile Glu
1               5

<210> SEQ ID NO 34
<211> LENGTH: 17
<212> TYPE: PRT
<213> ORGANISM: Artificial Sequence
<220> FEATURE:
<223> OTHER INFORMATION: Synthetic_CDR-H2 of anti-CD40 antibody

<400> SEQUENCE: 34

Val Ile Asn Pro Gly Tyr Gly Gly Val Asn Tyr Asn Glu Lys Phe Lys
1               5                   10                  15

Gly

<210> SEQ ID NO 35
<211> LENGTH: 11
<212> TYPE: PRT
<213> ORGANISM: Artificial Sequence
<220> FEATURE:
<223> OTHER INFORMATION: Synthetic_CDR-L1 of anti-CD40 antibody

<400> SEQUENCE: 35

Arg Ala Ser Gln Asp Ile Ser Asn His Leu Asn
1               5                   10

<210> SEQ ID NO 36
<211> LENGTH: 7
<212> TYPE: PRT
<213> ORGANISM: Artificial Sequence
<220> FEATURE:
<223> OTHER INFORMATION: Synthetic_CDR-L2 of anti-CD40 antibody
```

```
<400> SEQUENCE: 36

Ser Thr Ser Arg Leu His Ser
1               5
```